US009907754B2

(12) United States Patent
Farrow et al.

(10) Patent No.: US 9,907,754 B2
(45) Date of Patent: Mar. 6, 2018

(54) TAURINE COMPOSITIONS SUITABLE FOR INHALATION

(71) Applicant: VECTURA LIMITED, Wiltshire (GB)

(72) Inventors: David Farrow, Wiltshire (GB); Katie Coggins, Wiltshire (GB)

(73) Assignee: VECTURA LIMITED, Wiltshire (GB)

( * ) Notice: Subject to any disclaimer, the term of this patent is extended or adjusted under 35 U.S.C. 154(b) by 0 days.

(21) Appl. No.: 15/488,616

(22) Filed: Apr. 17, 2017

(65) Prior Publication Data

US 2017/0281546 A1 Oct. 5, 2017

Related U.S. Application Data

(62) Division of application No. 14/779,156, filed as application No. PCT/GB2014/050953 on Mar. 26, 2014, now abandoned.

(30) Foreign Application Priority Data

Mar. 28, 2013 (GB) .................................. 1305813.6

(51) Int. Cl.

| | |
|---|---|
| ***A61K 9/16*** | (2006.01) |
| ***A61K 9/00*** | (2006.01) |
| ***A61K 45/06*** | (2006.01) |
| ***A61K 31/58*** | (2006.01) |
| ***A61K 31/185*** | (2006.01) |
| ***A61K 31/40*** | (2006.01) |
| ***A61K 31/137*** | (2006.01) |
| ***A61K 31/167*** | (2006.01) |
| ***A61K 31/439*** | (2006.01) |
| ***A61K 31/4704*** | (2006.01) |
| ***C07C 303/42*** | (2006.01) |
| ***C07C 309/14*** | (2006.01) |
| ***A61K 31/138*** | (2006.01) |

(52) U.S. Cl.

CPC ............ *A61K 9/1617* (2013.01); *A61K 9/008* (2013.01); *A61K 9/0075* (2013.01); *A61K 9/1682* (2013.01); *A61K 31/137* (2013.01); *A61K 31/138* (2013.01); *A61K 31/167* (2013.01); *A61K 31/185* (2013.01); *A61K 31/40* (2013.01); *A61K 31/439* (2013.01); *A61K 31/4704* (2013.01); *A61K 31/58* (2013.01); *A61K 45/06* (2013.01); *C07C 303/42* (2013.01); *C07C 309/14* (2013.01)

(58) Field of Classification Search

CPC .............. A61K 2300/00; A61K 31/137; A61K 31/138; A61K 31/167; A61K 31/40; A61K 31/439; A61K 31/4704; A61K 31/58; A61K 31/185; A61K 45/06; A61K 9/0075; A61K 9/008; A61K 9/1617; A61K 9/1682; C07C 303/42; C07C 309/14

See application file for complete search history.

(56) References Cited

U.S. PATENT DOCUMENTS

| | | | | |
|---|---|---|---|---|
| 6,257,233 | B1 | 7/2001 | Burr et al. | |
| 2008/0286369 | A1* | 11/2008 | Moore ................ | A61K 9/0019 424/490 |

FOREIGN PATENT DOCUMENTS

| | | |
|---|---|---|
| CN | 1872029 | 12/2006 |
| CN | 100398096 | 7/2008 |
| CN | 101671283 | 9/2009 |
| JP | 07304725 | 11/1995 |
| JP | 1160476 | 3/1999 |
| WO | 1992017170 | 10/1992 |
| WO | 1996032149 | 10/1996 |
| WO | 200100262 | 1/2001 |
| WO | 200207805 | 1/2002 |
| WO | 2002089880 | 11/2002 |
| WO | 2002089881 | 11/2002 |
| WO | 2010086285 | 12/2011 |

OTHER PUBLICATIONS

Kudos et al. "Production of fine organic crystalline particles by using milli segmented flow crystallizer." Journal of Chemical Engineering of Japan 2012 Society of Chemical Engineers, Japan, vol. 45, No. 4, 2012, pp. 305-309.
International Search Report and Written Opinion of PCT/GB14/50953 dated Jun. 25, 2014.
Intellectual Property Office Search Report for GB1305813.6 dated Aug. 23, 2013.

* cited by examiner

*Primary Examiner* — Michael B. Pallay
(74) *Attorney, Agent, or Firm* — Matthew S. Gibson; Reed Smith LLP

(57) ABSTRACT

The invention discloses spray-dried compositions for inhalation and methods for preparing such powder compositions. The compositions of the invention are produced by spray-drying taurine under conditions that (i) retain the physical and chemical stability of the composition during spray drying and upon storage, (ii) protect the powder composition from aggregation and (iii) provide particles suitable for aerosolization.

20 Claims, 16 Drawing Sheets pH profile and isoelectric point of taurine

FIG. 9

Joint Factor Tests

| Term | DF | Sum of Squares | F Ratio | Prob > F |
|---|---|---|---|---|
| Feedstock Concentration (%w/v) | 4 | 10665.73 | 20032.44 | 0.0053* |
| Drying Gas (kg/hr) | 4 | 35688.84 | 67030.96 | 0.0029* |
| Outlet Temperature (°C) | 6 | 219933.88 | 275387.3 | 0.0015* |
| Feedrate (g/min) | 5 | 82431.94 | 123859.3 | 0.0022* |
| Feedstock Temperature (°C) | 5 | 128944.38 | 193747.2 | 0.0017* |
| Solution pH | 5 | 80610.74 | 121122.8 | 0.0022* |
| Atomisation Flow Rate (l/min) | 6 | 200972.45 | 251645.0 | 0.0015* |

PSD – Tre/Leu/Sal - Process A – Initial Time Point, T=0 hours:

PSD – Tre/Leu/Sal - Process A - Stored under ambient sealed conditions - T=24 hours:

PSD -- Tau/Leu/Sal - Process B - Stored under ambient sealed conditions - T=24 hours:

PSD – Tre/Leu/Sal - Process B – Initial Time Point, T=0 hours:

PSD – Tre/Leu/Sal - Process B - Stored under ambient sealed conditions - T=24 hours:

PSD – Tau/Leu/Sal - Process B – Stored open at 25°C/50%RH - T=24 hours

TAURINE COMPOSITIONS SUITABLE FOR INHALATION

RELATED APPLICATIONS

This application is a divisional of U.S. patent application Ser. No. 14/779,156, filed Sep. 22, 2015, which is a United States national stage of International Application No. PCT/GB2014/050953, filed Mar. 26, 2014, which was published as International Publication No. WO 2014/155103 A1, and which claims benefit of United Kingdom Application No. 1305813.6 filed, Mar. 28, 2013, the entire contents of which are hereby expressly incorporated herein by reference thereto.

DESCRIPTION

The present invention relates to stable materials, compositions comprising such materials suitable for inhalation and methods for preparing such compositions.

BACKGROUND OF THE INVENTION

The process of spray drying has been widely used in the production of pharmaceuticals since the 1940s (Corrigan, 1995). The food industry also commonly employs spray drying to produce food products demonstrating enhanced stability and suitable for long term storage (Sliwinski et al., 2004). Spray drying is a one step process used to convert a liquid based feedstock (such as a solution, suspension or emulsion) into a dried powder form by atomizing the feedstock in droplets, into a hot drying-medium, typically air or nitrogen. The process provides enhanced control over particle size, size distribution, particle shape, density, purity and structure. As formulators are able to control these parameters so precisely, spray drying as a possible method for formulating dry powder compositions intended for pulmonary delivery has also been investigated in recent years (WO 96/32149).

Spray drying active pharmaceutical ingredients (API) or biological material suitable for inhalation normally requires the presence of stabilizing excipients and/or diluents.

The de-facto spray drying excipient of choice is often Mannitol as it possesses many advantageous properties. Mannitol will readily dry in a crystalline state, is water soluble and is considered non-hygroscopic as it picks up less than 1% moisture at relative humidity as high as 70% (Handbook of Pharmaceutical Excipients, $6^{th}$ Edition, R. C. Rowe). In addition it can pick up 10% of mass in water at humidity's >70% RH. However despite mannitol's attractive stabilizing capabilities, it is a tussive agent and will induce coughing when administered via the pulmonary route.

As an alternative choice excipient, trehalose is often used for spray drying compositions. Trehalose (α-D-glucopyranosyl-α-D-glucopyranoside) is a naturally occurring, non-reducing disaccharide which was initially found to be associated with the prevention of desiccation damage in certain plants and animals which can dry out without damage and can revive when rehydrated. Trehalose however does not spray dry completely crystalline and will instead form an amorphous matrix. This amorphous matrix is hygroscopic and will readily absorb water. Spray-dried trehalose therefore suffers from physical stability issues, principally particle agglomeration, resulting in loss of primary particle size and aerosol performance characteristics.

Thus a need still exists for materials such as excipients for preparing stable inhalable compositions which exhibit excellent aerosolisation properties and demonstrate very low levels of agglomeration. Ideally, such excipients will spray dry in a crystalline form and will possess various favourable attributes such as low toxicity (with no cough induced side effects), low hygroscopicity, high melting point, with very low moisture content (advantageous for long term storage).

SUMMARY OF THE INVENTION

The invention relates to a method for preparing conditioned taurine, the method comprising a conditioning step, optionally a spray drying step, to produce taurine that:

(a) demonstrates no significant net change in the $D_{90}$ (±20%) after 7 days of ambient storage; and (b) have a particle size ($D_{90}$) of <20 μm, but more preferably <10 μm after 7 days of ambient storage, optionally and preferably in which a method zwitterionic neutralisation is facilitated during spray drying of the taurine.

The invention also relates to conditioned taurine, obtained or obtainable by the method of the invention and to a composition comprising conditioned taurine, such as a dry powder composition suitable for inhalation.

The invention further relates to a method for preparing conditioned taurine the method comprising drying solubilised taurine, optionally by spray drying with one or more of the following parameters:

(a) the pH of the feedstock to be spray dried is acidic e.g. less than pH 5, preferably equal to or less then pH 4, such as about pH 4;

(b) wherein the feedstock concentration is between 0.1% and 10%, more preferably between 1% and 5%;

(c) the feedstock temperature is between 0.1° C. and 100° C., more preferably between 20° C. and 70° C.;

(d) the outlet temperature is between 50° C. and 120° C., more preferably between 60° C. and 100° C.;

(e) the $T_{(solid:gas)}$ ratio is between $2.000\times10^{-6}$ and $2.750\times10^{-3}$.

The invention also relates to a container comprising:

(a) conditioned taurine; or (b) a composition comprising conditioned taurine.

The invention also relates to a method for preparing conditioned taurine, the method being a multi-step process, in one embodiment a two-step process, and in one further embodiment a one step process such as spray drying.

FIGURES

FIG. 9 lists the joint factor tests indicating significance of all variables.

Figure 10:
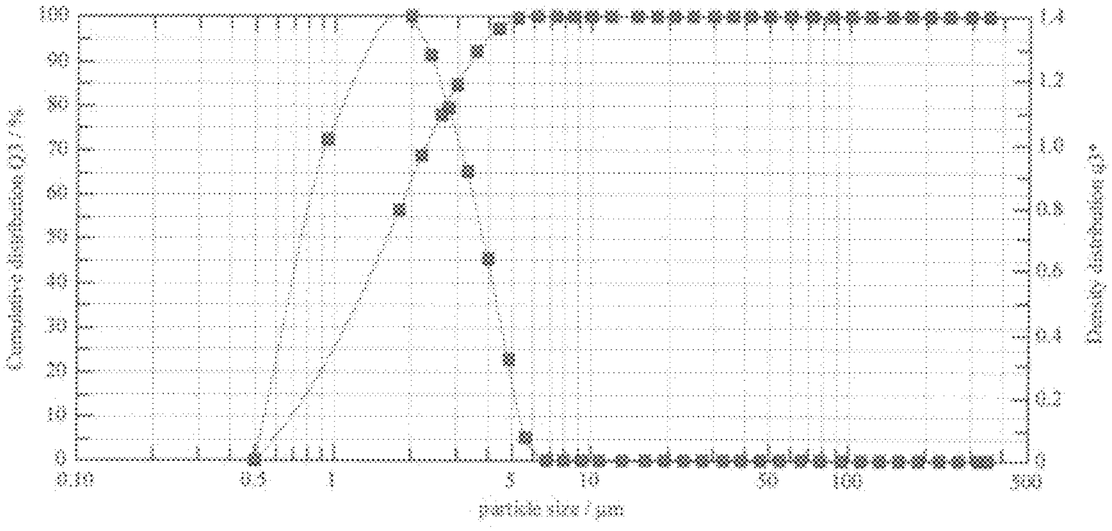

FIG. 10 is a graph depicting the PSD (particle size distribution) for a spray-dried trehalose/leucine/salbutamol powder composition obtained by spray-drying under Process A conditions where T=0.

Figure 11:
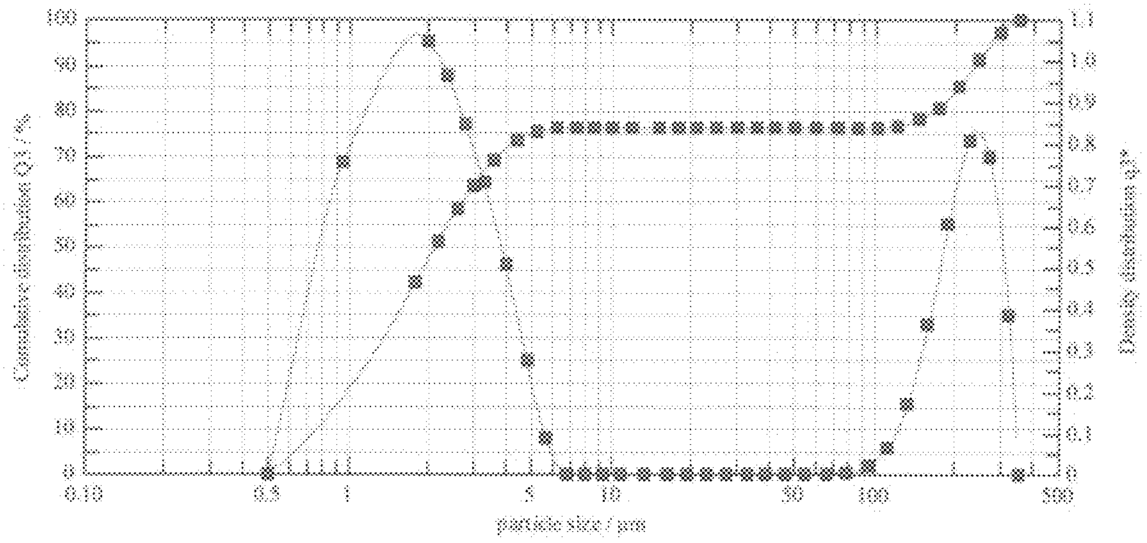

FIG. 11 is a graph depicting the PSD (particle size distribution) for a spray-dried trehalose/leucine/salbutamol powder composition obtained by spray-drying under Process A, stored under ambient sealed conditions where T=24 hours.

Figure 12:
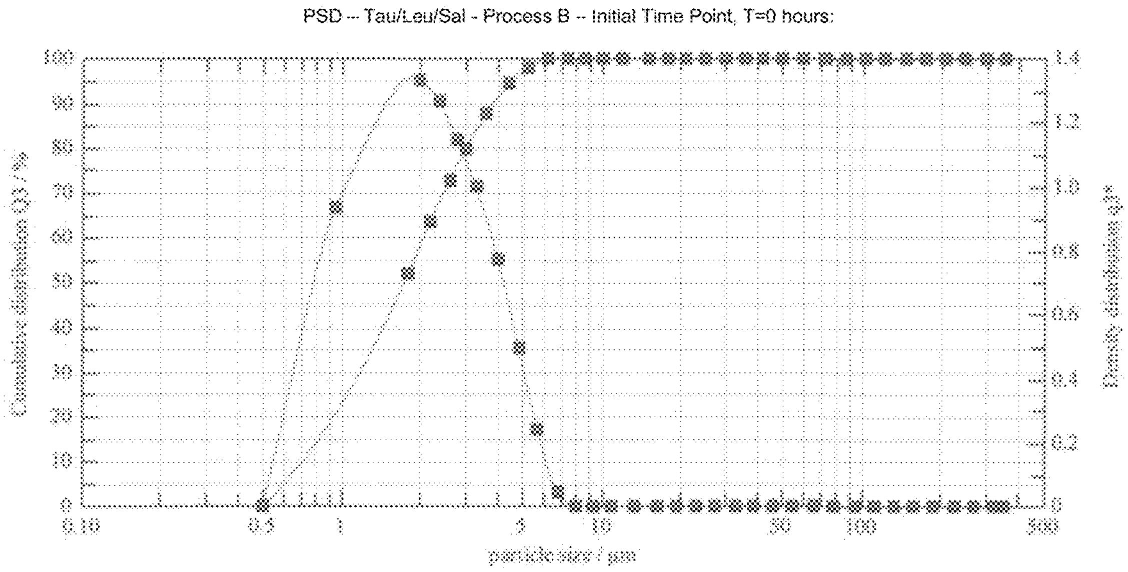

FIG. 12 is a graph depicting the PSD (particle size distribution) for a spray-dried taurine/leucine/salbutamol powder composition obtained by spray-drying under Process B conditions where T=0.

Figure 13:
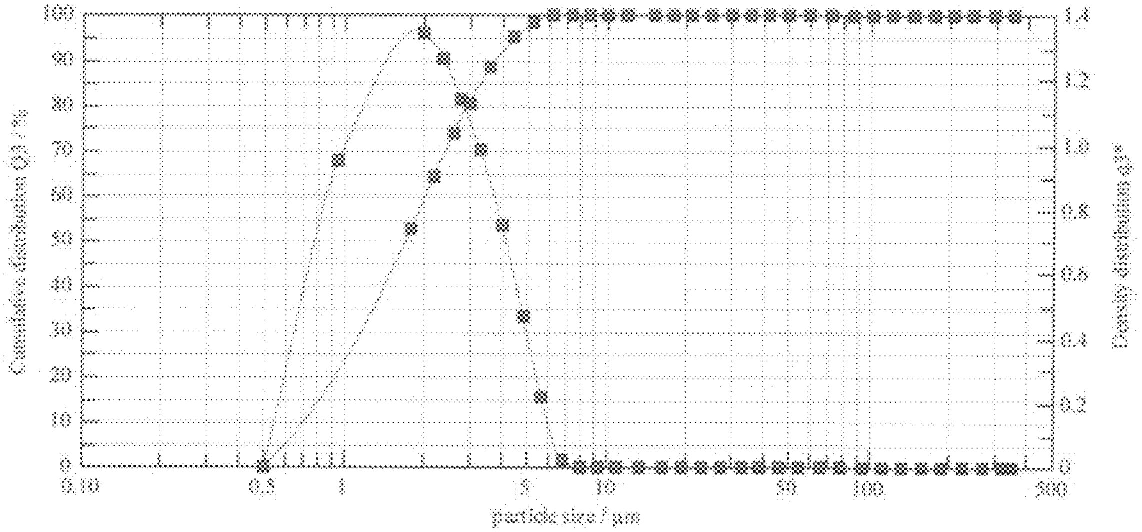

FIG. 13 is a graph depicting the PSD (particle size distribution) for a spray-dried taurine/leucine/salbutamol powder composition obtained by spray-drying under Process B, stored under ambient sealed conditions where T=24 hours.

Figure 14:
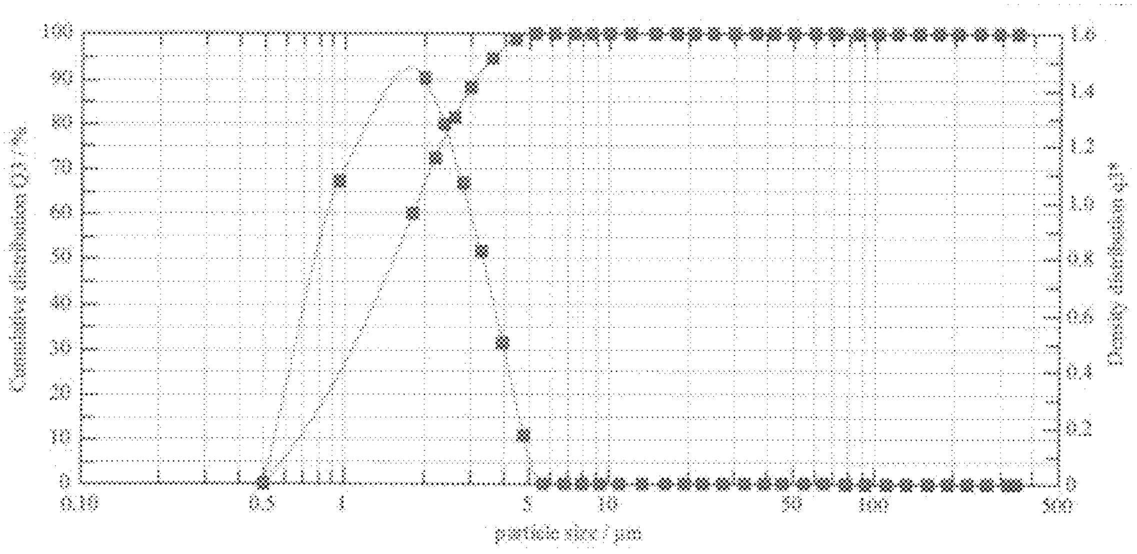

FIG. 14 is a graph depicting the PSD (particle size distribution) for a spray-dried trehalose/leucine/salbutamol powder composition obtained by spray-drying under Process B conditions where T=0.

Figure 15:
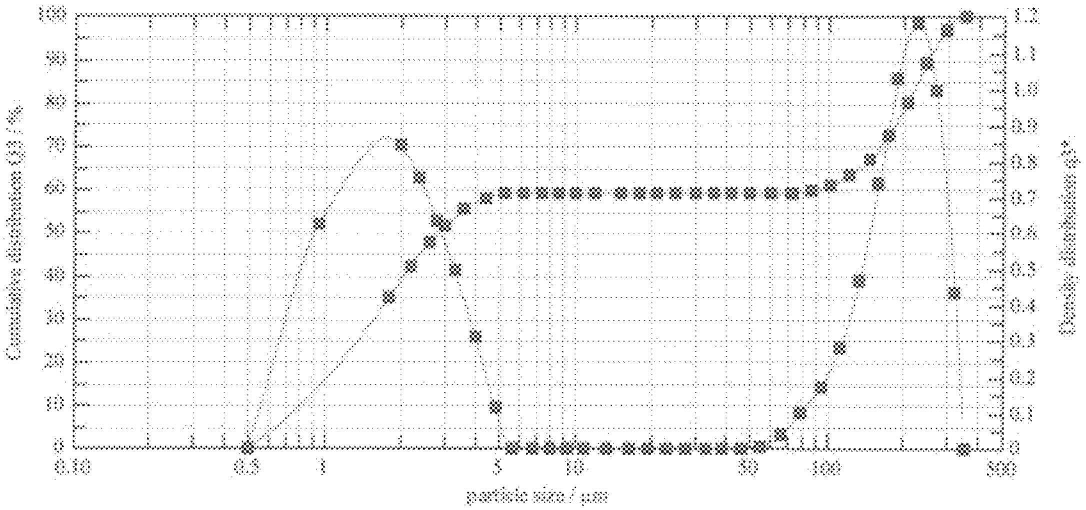

FIG. 15 is a graph depicting the PSD (particle size distribution) for a spray-dried trehalose/leucine/salbutamol powder composition obtained by spray-drying under Process B, stored under ambient sealed conditions where T=24 hours.

Figure 16:
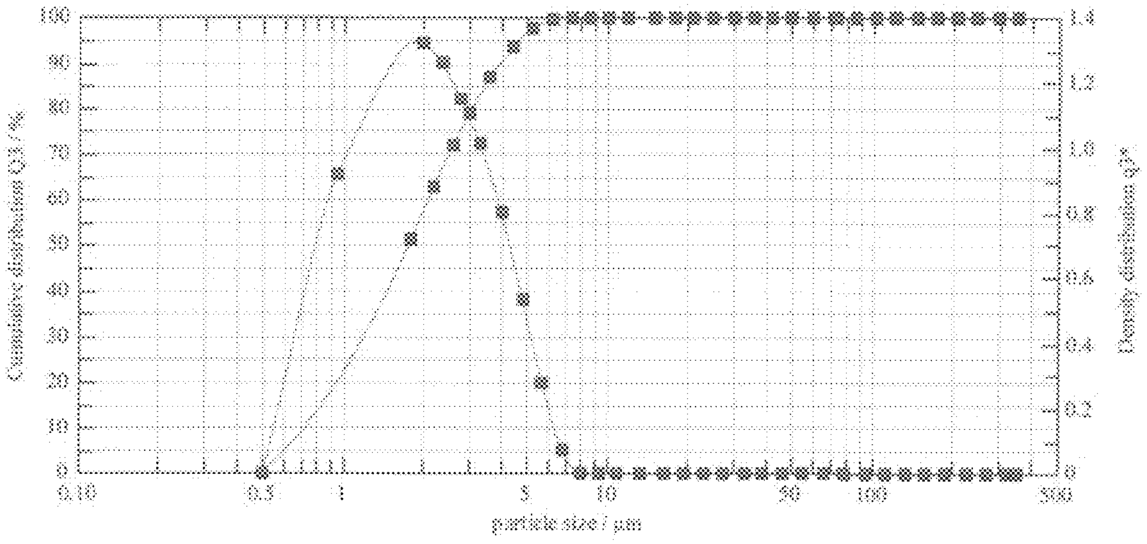

FIG. 16 is a graph depicting the PSD (particle size distribution) for a spray-dried taurine/leucine/salbutamol powder composition obtained by spray-drying under Process B, stored open at 25° C./50% RH, where T=24 hours.

DETAILED DESCRIPTION OF THE INVENTION

Taurine or 2-aminoethanesulfonic acid is an organic acid that is ubiquitous in the human body, constituting 0.1% w/w of its total weight (EFSA Response Letter, EFSA-Q-2007-113, 2009). It has been shown to be tolerable in excess of 1000 mg $kg^{-1}$ $day^{-1}$ by the EFSA with no indications of inhalation toxicity or intolerability. Taurine has exceptionally low moisture sorption characteristics and is thus considered non-hygroscopic as it does not take up any water at a relative humidity of between 0% and 100%. It is also soluble in water, is not considered a tussive agent and when spray-dried, produces particles with very low moisture content (less than 1% w/w, more preferably less than 0.5% w/w).

Taurine is a versatile molecule with various important biological functions, including: antioxidation; conjugation of bile acids; modulation of calcium signalling; osmoregulation and membrane stabilization. Taurine is also regularly used as a dietary supplement and as an ingredient in energy drinks.

Although there is little evidence in the literature of taurine being utilised as an active pharmaceutical ingredient, it has been described for the treatment of cardiac failure, and a taurine based composition has been disclosed in the treatment of asthma and various other respiratory failures (WO 92/17170). In the latter example, the taurine based composition was administered by pulmonary inhalation as an aerosolised solution.

Spray drying taurine to create inhalable taurine particles that do not agglomerate has proven surprisingly challenging.

In the present invention we have determined spray drying taurine under certain conditions can result in particle agglomeration over 1 to 7 days resulting in a loss of primary particles and negligible aerosol performance.

However, under certain conditions taurine can be produced which is suitable for inhalation use, and does not display such agglomeration. Such taurine is referred to as conditioned taurine herein, and in one aspect is made by the methods of the invention as disclosed herein, although other methods can be used. Conditioned taurine is suitably taurine that demonstrates no significant net change in the $D_{90}$ (±20%) after 7 days of ambient storage and has a particle size ($D_{90}$) of <20 μm, but more preferably <10 μm after 7 days of ambient storage.

Provided herein is also a likely basis for the agglomeration of taurine which permits conditioned taurine to be produced by spray drying and other methods, the basis referred to herein as the zwitterionic neutralisation theory.

Definitions

It will be understood that particular embodiments described herein are shown by way of illustration and not as limitations of the invention. The principal features of this invention can be employed in various embodiments without departing from the scope of the invention. Those skilled in the art will recognise, or be able to ascertain using no more than routine study, numerous equivalents to the specific procedures described herein. Such equivalents are considered to be within the scope of this invention and are covered by the claims.

The term "Taurine" is intended to encompass salt forms or counterion formulations of taurine as well as isolated stereoisomers (e.g. D-Taurine or L-Taurine) and mixtures of stereoisomers. Derivatives and intermediates of taurine (e.g. hypotaurine) are also encompassed.

The term "Raw Taurine" refers to commercially available pure taurine.

The term "Processed Taurine" refers to taurine that has been spray-dried using spray drying conditions with resulting taurine particles tending to agglomerate (i.e. demonstrate a net change in the $D_{90}$ (>20%) after 7 days of ambient storage) and have a particle size ($D_{90}$) of >20 μm after 7 days of ambient storage.

The term "Conditioned Taurine" refers to taurine that has been prepared to obtain taurine particles that demonstrate very low levels of agglomeration (i.e. demonstrate no significant net change in the $D_{90}$ (±20%) after 7 days of ambient storage) and remain as aerosolisable primary particles e.g. where particles have a particle size ($D_{90}$) of <20 μm, but more preferably <10 μm after 7 days of ambient storage.

The term "Leucine" is intended to encompass salt forms or counterion formulations of leucine as well as isolated stereoisomers (e.g. D-Leucine or L-Leucine) and mixtures of stereoisomers. Derivatives and intermediates of leucine are also encompassed.

The term "Agglomerate" or "Agglomeration" refers to the process whereby particles cohere to one another to create particle clusters, which demonstrate larger particle dimensions.

The term "Aerosolised" or "Aerosolisable" refers to particles, which when dispensed from a dry powder inhalation device, will remain suspended in the inhaler's gas stream for an amount of time suitable for at least a portion of the particles to be inhaled by the patient, thereby reaching the patients lungs.

The term "Process Parameters" refers specifically to spray drying parameters such as: drying gas flow rate; atomisation gas flow rate; feedstock pumping rate; outlet temperature; feedstock temperature; feedstock concentration and feedstock pH and buffer/acid type.

The term "$D_{10}$" refers to the size in microns below which 10% of the particles reside on a volume basis.

The term "$D_{50}$" refers to the size in microns above or below which 50% of the particles reside on a volume basis.

The term "$D_{90}$" refers to the size in microns below which 90% of the particles reside on a volume basis.

The term "Inhalation" or "Inhalable" refers to particles that are suitable for pulmonary administration. Such particles typically have a mean aerodynamic particle size of less than 10 μm, more preferably less than 5 μm and most preferably less than 3.5 μm.

The term "Process A" refers to a preferred spray drying process for producing optimal trehalose particles suitable for inhalation using in one embodiment the Niro spray dryer.

The term "Process B" refers to a preferred spray drying process for producing optimal taurine particles, namely conditioned taurine particles suitable for inhalation using in one embodiment the Niro spray dryer.

The term "Ambient Conditions" refers to material sealed and stored at room temperature at about 20° C.±2.0° C. in the laboratory.

The term "Medicament" refers to pharmaceutical active agents or bioactive material. Medicament may also refer to combinations of pharmaceutical agents, combinations of bioactive material or combinations of pharmaceutical agent and bioactive material.

The term "Container" refers to either a bulk storage container, such as a multi-dose reservoir for a dry powder inhaler, or unit dose containers such as a capsule or a blister. The capsule may be formed from various materials e.g. gelatine, cellulose derivatives such as hydroxypropyl methylcellulose (HPMC) or hydroxypropylcellulose (HPC), starch, starch derivatives, chitosan or synthetic plastics, while the blister may be provided in the form of a blister pack or blister strip.

The term "Passive Device" refers to a dry powder inhaler device in which a patient's breathe is the only source of gas which provides the motive force in the device.

The term "Active Device" refers to a dry powder inhaler device in which a source of compressed gas or an alternative energy source is used to provide the motive force in the device.

The term "Glass Transition Temperature", which is represented by the symbol $T_9$, refers to the temperature at which a composition changes from a glassy or vitreous state to a syrup or rubbery state. $T_9$ is generally determined using differential scanning calorimetry (DSC).

The term "$T_{(solid:gas)}$ ratio" refers to the mass of taurine per volume of drying gas per unit time in the spray dryer.

General Statements

As used in this specification and the claim(s), the use of the word "a" or "an" when used in conjunction with the term "comprising" in the claim(s) and/or the specification may mean "one", but it is also consistent with the meaning of "one or more", "at least one", and "one or more than one". The use of the term "or" in the claim(s) is used to mean "and/or" unless explicitly indicated to refer to alternatives only or the alternatives are mutually exclusive, although the disclosure supports a definition that refers to only alternatives and "and/or".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "any combinations thereof" as used herein refers to all permutations and mixtures of the listed items preceding the term. For example, "A, B, C, or any combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are mixtures that contain repeats of one or more items or terms, such as BB, AAA, BBC, AAABCCCC, CBBAAA, CABABB, and so forth. The skilled artisan will understand that typically there 525 is no limit on the number of items or terms in any mixture, unless otherwise apparent from the context.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

DETAILED DESCRIPTION

Process

The invention relates to, inter alia, a method for preparing taurine, the method comprising a conditioning step, wherein taurine is produced in the form of particles that:

(a) demonstrate no significant net change in the $D_{90}$ (±20%) after 7 days of ambient storage; and (b) have a particle size ($D_{90}$) of <20 μm, but more preferably <10 μm after 7 days of ambient storage, optionally and preferably in which a method zwitterionic neutralisation is facilitated during drying of the taurine.

As taurine is a zwitterionic compound, it is believed that the sulphur-hydyl group of the taurine becomes ionised (oxidation) with the proton being added to the amine group (reduction), in the feedstock of a spray drying approach, and retains a charge even after drying. This leads to the material relaxing on storage which is believed to be the charged groups neutralising resulting in a conformatorial structural change. This conformatorial change causes agglomeration of the particles in the dry state, leading to a significant reduction in the aerosol performance. It is believed the neutralisation has a vitrification intermediate phase, which is the cause of the agglomeration.

In one aspect facilitation of zwitterionic neutralisation is the prevention or minimising of ionic interaction between the sulphur-hydyl group of the taurine and the amine group, such as the use of conditions that minimise or prevent reduction of the amine group and/or oxidation of the sulphur-hydyl group.

Further, we have demonstrated in the examples herein that predictive models can be generated that allow modulation of the spray drying parameters consistent with this theory to allow conditioned taurine as defined herein to be produced.

Parameters that affect the zwitterionic neutralisation process include:

Drying Gas flow rate
Atomisation gas flow rate
Feedstock pumping rate
Outlet temperature
Feedstock temperature
Feedstock concentration
Feedstock pH and buffer/acid type Thus in one aspect of the invention any one or more of the above parameters may be varied to allow conditioned taurine to be produced, and the invention relates to a method for spray drying taurine, wherein one or more or all of these properties are controlled to produce conditioned taurine, optionally wherein a model using one or more or all parameters is used to predict appropriate parameters for the production of conditioned taurine.

In one embodiment of the invention the taurine is spray dried.

In one embodiment of the invention the pH of the feedstock to be spray dried is acidic e.g. less than pH 5 in one embodiment equal to or less then pH 4, such as about pH 4.

In a further aspect of the invention the feedstock concentration is between 0.1% and 10%, in one embodiment between 1% and 5%.

In another aspect of the invention the feedstock temperature is between 0.1° C. and 100° C., in one embodiment between 20° C. and 70° C.

In still a further aspect of the invention the outlet temperature is between 50° C. and 120° C., in one embodiment between 60° C. and 100° C.

In another aspect of the invention the $T_{(solid:gas)}$ ratio is between $2.000\times10^{-6}$ and $2.750\times10^{-3}$.

The production of conditioned taurine can be confirmed by:

(a) no significant net change in the $D_{90}$ (±20%) after 7 days of ambient storage; and (b) a particle size ($D_{90}$) of <20 μm, but more preferably <10 μm after 7 days of ambient storage following the drying process.

In a further aspect of the invention raw commercially available taurine may be comminuted to reduce particle size before any processing to produce conditioned taurine as described herein. Particle size reduction is preferably to form a particle of size less than 20 μm in diameter, in one embodiment less than 10 μm in diameter.

Comminution can be achieved through various processes in isolation, for example media milling or jet milling (micronisation).

Conditioning is the process of allowing charge neutralisation induced, for example following the communition step.

For the avoidance of doubt the conditioning of taurine may be carried out by spray drying but other techniques may also be used to produce conditioned taurine, such as fluid bed conditioning. Fluid bed conditioning is considered a one-step conditioning process but would additionally require a separate communition step and so a preferred method to achieve both the conditioned step and the communition step simultaneously, repeatably and more economically is to use spray drying.

The method of preparing conditioned taurine may therefore involve a multi-step process, or in one embodiment a two-step process or in one further embodiment a one-step process such as spray drying.

Spray drying solubilises the taurine raw material and produces smaller particles through atomisation, which in this sense, due to the size reduction, is considered as comminuted.

In a further aspect of the present invention, the conditioned taurine is made by a spray drying method comprising: providing a feedstock comprising raw taurine in an aqueous solution or suspension, and spray drying the feedstock under conditions to create particles that demonstrate no significant net change in the $D_{90}$ (±20%) after 7 days of ambient storage; and havea particle size ($D_{90}$) of <20 μm, but more preferably <10 μm after 7 days of ambient storage.

Product

The invention relates to conditioned taurine obtained or obtainable using the method of the invention, and to compositions comprising such taurine per se.

For example, the invention relates to a composition comprising conditioned taurine, such as a dry powder composition suitable for inhalation.

In one embodiment the conditioned taurine is substantially in crystalline form, with at least 95% of the taurine or more having a crystalline form In one embodiment of the invention, the conditioned taurine is present in an amount less than 99.9% by weight based on the dry weight of the composition e.g. less than 98.5%, less than 90%, less than 80%, less than 70%, less than 60%, less than 50%, less than 40%, less than 30%, less than 20%, less than 10%, less than 5%, less than 2.5% by weight based on the dry weight of the composition.

In a further embodiment of the invention, taurine has a moisture content of less than 2% by weight, optionally less than 1% by weight, optionally less than 0.5% by weight of conditioned taurine.

Compositions and Other Elements

In another embodiment of the present invention, the conditioned taurine is both suitable for use as, and for use as an excipient, carrier or diluent in a pharmaceutical composition.

The taurine of the invention may be prepared in combination with other components, such as drugs or excipients, for example in a co-spray dried process.

In one embodiment the taurine may be dried, e.g. co-spray dried with leucine in an aqueous solution or suspension, wherein the aqueous solution or suspension is spray dried under conditions to produce a composition comprising conditioned taurine and leucine suitable for inhalation.

In one embodiment the spray-dried composition comprising leucine will comprise leucine present in an amount less than 10% by weight based on the dry weight of the composition e.g. less than 9%, less than 8%, less than 7%, less than 6%, less than 5%, in one embodiment less than 4%, in one embodiment less than 3%, in one embodiment less than 2% by weight based on the dry weight of the composition.

In one embodiment of the present invention, a composition comprising taurine may also comprise an additive material such as a so-called force control agent. A force control agent is an agent which reduces the cohesion between fine particles within the powder composition. Suitable force control agents include amino acids, metal stearates such as magnesium stearate, phospholipids, lecithin, colloidal silicon dioxide and sodium stearyl fumarate. In one embodiment the force control agent is magnesium stearate.

Amino acids which are suitable for use in the present invention include alanine, leucine, isoleucine, lysine, valine, methionine or phenylalanine. In one embodiment the amino acid is leucine. The inclusion of these amino acids improves the aerosol performance of the composition.

In yet a further embodiment of the present invention, the amino acid, in one embodiment leucine, is present in an amount less than 10% by weight based on the dry weight of the composition e.g. less than 9%, less than 8%, less than 7%, less than 6%, less than 5%, in one embodiment less than 4%, in one embodiment less than 3%, in one embodiment less than 2% by weight based on the dry weight of the composition.

In still a further embodiment of the present invention, the amino acid is predominately present on the surface of the conditioned taurine. Without wishing to be bound by theory this may result from the amino acid's hydrophobic and surface active properties.

Actives

In yet a further aspect of the present invention, the composition further comprises a medicament or a combination of medicaments selected from the following:

1) Adrenergic agonists such as, for example, amphetamine, apraclonidine, bitolterol, clonidine, colterol, dobutamine, dopamine, ephedrine, epinephrine, ethylnorepinephrine, fenoterol, formoterol, guanabenz, guanfacine, hydroxyamphetamine, isoetharine, isoproterenol, isotharine, mephenterine, metaraminol, methamphetamine, methoxamine, methpentermine, methyldopa, methylphenidate, metaproterenol, metaraminol, mitodrine, naphazoline, norepinephrine, oxymetazoline, pemoline, phenylephrine, phenylethylamine, phenylpropanolamine, pirbuterol, prenalterol, procaterol, propylhexedrine, pseudoephedrine, ritodrine, salbutamol, salmeterol, terbutaline, tetrahydrozoline, tramazoline, tyramine and xylometazoline.

2) Adrenergic antagonists such as, for example, acebutolol, alfuzosin, atenolol, betaxolol, bisoprolol, bopindolol, bucindolol, bunazosin, butyrophenones, carteolol, carvedilol, celiprolol, chlorpromazine, doxazosin, ergot alkaloids, esmolol, haloperidol, indoramin, ketanserin, labetalol, levobunolol, medroxalol, metipranolol, metoprolol, nebivolol, nadolol, naftopidil, oxprenolol, penbutolol, phenothiazines, phenoxybenzamine, phentolamine, pindolol, prazosin, propafenone, propranolol,sotalol, tamsulosin, terazosin, timolol, tolazoline, trimazosin, urapidil and yohimbine.

3) Adrenergic neurone blockers such as, for example, bethanidine, debrisoquine, guabenxan, guanadrel, guanazodine, guanethidine, guanoclor and guanoxan.

4) Drugs for treatment of addiction, such as, for example, buprenorphine.

5) Drugs for treatment of alcoholism, such as, for example, disulfiram, naloxone and naltrexone.

6) Drugs for Alzheimer's disease management, including acetylcholinesterase inhibitors such as, for example, donepezil, galantamine, rivastigmine and tacrin.

7) Anaesthetics such as, for example amethocaine, benzocaine, bupivacaine, hydrocortisone, ketamine, lignocaine, methylprednisolone, prilocaine, proxymetacaine, ropivacaine and tyrothricin.

8) Angiotensin converting enzyme inhibitors such as, for example, captopril, cilazapril, enalapril, fosinopril, imidapril hydrochloride, lisinopril, moexipril hydrochloride, perindopril, quinapril, ramipril and trandolapril.

9) Angiotensin receptor blockers, such as, for example, candesartan, cilexetil, eprosartan, irbesartan, losartan, medoxomil, olmesartan, telmisartan and valsartan.

10) Antiarrhythmics such as, for example, adenosine, amidodarone, disopyramide, flecainide acetate, lidocaine hydrochloride, mexiletine, procainamide, propafenone and quinidine.

11) Antibiotic and antibacterial agents (including the beta-lactams, fluoroquinolones, ketolides, macrolides, sulphonamides and tetracyclines) such as, for example, aclarubicin, amoxicillin, amphotericin, azithromycin, aztreonam chlorhexidine, clarithromycin, clindamycin, colistimethate, dactinomycin, dirithromycin, doripenem, erythromycin, fusafungine, gentamycin, metronidazole, mupirocin, natamycin, neomycin, nystatin, oleandomycin, pentamidine, pimaricin, probenecid, roxithromycin, sulphadiazine and triclosan.

12) Anti-clotting agents such as, for example, abciximab, acenocoumarol, alteplase, aspirin, bemiparin, bivalirudin, certoparin, clopidogrel, dalteparin, danaparoid, dipyridamole, enoxaparin, epoprostenol, eptifibatide, fondaparin, heparin (including low molecular weight heparin), heparin calcium, lepirudin, phenindione, reteplase, streptokinase, tenecteplase, tinzaparin, tirofiban and warfarin.

13) Anticonvulsants such as, for example, GABA analogs including tiagabine and vigabatrin; barbiturates including pentobarbital; benzodiazepines including alprazolam, chlordiazepoxide, clobazam, clonazepam, diazepam, flurazepam, lorazepam, midazolam, oxazepam and zolazepam; hydantoins including phenytoin; phenyltriazines including lamotrigine; and miscellaneous anticonvulsants including acetazolamide, carbamazepine, ethosuximide, fosphenytoin, gabapentin, levetiracetam, oxcarbazepine, piracetam, pregabalin, primidone, sodium valproate, topiramate, valproic acid and zonisamide.

14) Antidepressants such as, for example, tricyclic and tetracyclic antidepressants including amineptine, amitriptyline (tricyclic and tetracyclic amitryptiline), amoxapine, butriptyline, cianopramine, clomipramine, demexiptiline, desipramine, dibenzepin, dimetacrine, dosulepin, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIS) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, a-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including acetaphenazine, ademetionine, S-adenosylmethionine, adrafinil, amesergide, amineptine, amperozide, benactyzine, benmoxine, binedaline, bupropion, carbamazepine, caroxazone, cericlamine,cotinine, fezolamine, flupentixol, idazoxan, kitanserin, levoprotiline, lithium salts, maprotiline, medifoxamine, methylphenidate, metralindole, minaprine, nefazodone,nisoxetine, nomifensine, oxaflozane, oxitriptan, phenyhydrazine, rolipram, roxindole, sibutramine, teniloxazine, tianeptine, tofenaci'n, trazadone, tryptophan, viloxazine and zalospirone.

15) Anticholinetgic agents such as, for example, atropine, benzatropine, biperiden, cyclopentolate, glycopyrrolate, hyoscine, ipratropium bromide, orphenadine hydrochloride, oxitroprium bromide, oxybutinin, pirenzepine, procyclidine, propantheline, propiverine, telenzepine, tiotropium, trihexyphenidyl, tropicamide and trospium.

16) Antidiabetic agents such as, for example, pioglitazone, rosiglitazone and troglitazone.

17) Antidotes such as, for example, deferoxamine, edrophonium chloride, fiumazenil, nalmefene, naloxone, and naltrexone.

18) Anti-emetics such as, for example, alizapride, azasetron, benzquinamide, bestahistine, bromopride, buclizine, chlorpromazine, cinnarizine, clebopride, cyclizine, dimenhydrinate, diphenhydramine, diphenidol, domperidone, dolasetron, dronabinol, droperidol, granisetron, hyoscine, lorazepam, metoclopramide, metopimazine, nabilone, ondansetron, palonosetron, perphenazine, prochlorperazine, promethazine, scopolamine, triethylperazine, trifluoperazine, triflupromazine, trimethobenzamide and tropisetron.

19) Antihistamines such as, for example, acrivastine, astemizole, azatadine, azelastine, brompheniramine, carbinoxamine, cetirizine, chlorpheniramine, cinnarizine, clemastine, cyclizine, cyproheptadine, desloratadine, dexmedetomidine, diphenhydramine, doxylamine, fexofenadine, hydroxyzine, ketotifen, levocabastine, loratadine, mizolastine, promethazine, pyrilamine, terfenadine and trimeprazine.

20) Anti-infective agents such as, for example, antivirals (including nucleoside and non-nucleoside reverse transcriptase inhibitors and protease inhibitors) including aciclovir, adefovir, amantadine, cidofovir, efavirenz, famiciclovir, foscarnet, ganciclovir, idoxuridine, indinavir, inosine pranobex, lamivudine, nelfinavir, nevirapine, oseltamivir, palivizumab, penciclovir, pleconaril, ribavirin, rimantadine, ritonavir, ruprintrivir, saquinavir, stavudine, valaciclovir, zalcitabine, zanamivir, zidovudine and interferons; AIDS adjunct agents including dapsone; aminoglycosides including tobramycin; antifungals including amphotericin, caspofungin, clotrimazole, econazole nitrate, fluconazole, itraconazole, ketoconazole, miconazole, nystatin, terbinafine and voriconazole; anti-malarial agents including quinine; antituberculosis agents including capreomycin, ciprofloxacin, ethambutol, meropenem, piperacillin, rifampicin and vancomycin; beta-lactams including cefazolin, cefmetazole, cefoperazone, cefoxitin, cephacetrile, cephalexin, cephaloglycin and cephaloridine; cephalosporins, including cephalosporin C and cephalothin; cephamycins such as cephamycin A, cephamycin, cephamycin C, cephapirin and cephradine; leprostatics such as clofazimine; penicillins including amoxicillin, ampicillin, amylpenicillin, azidocillin, benzylpenicillin, carbenicillin, carfecillin, carindacillin, clometocillin, cloxacillin, cyclacillin, dicloxacillin, diphenicillin, heptylpenicillin, hetacillin, metampicillin, methicillin, nafcillin, 2-pentenylpenicillin, penicillin N, penicillin 0, penicillin S and penicillin V; quinolones including ciprofloxacin, clinafloxacin, difloxacin, grepafloxacin, norfloxacin, ofloxacine and temafloxacin; tetracyclines including doxycycline and oxytetracycline; miscellaneous anti-infectives including linezolide, trimethoprim and sulfamethoxazole.

21) Anti-neoplastic agents such as, for example, droloxifene, tainoxifen and toremifene.

22) Antiparkisonian drugs such as, for example, amantadine, andropinirole, apomorphine, baclofen, benserazide, biperiden, benztropine, bromocriptine, budipine, cabergoline, carbidopa, eliprodil, entacapone, eptastigmine, ergoline, galanthamine, lazabemide, levodopa, lisuride, mazindol, memantine, mofegiline, orphenadrine, trihexyphenidyl, pergolide, piribedil, pramipexole, procyclidine, propentofylline, rasagiline, remacemide, ropinerole, selegiline, spheramine, terguride and tolcapone.

23) Antipsychotics such as, for example, acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine and zuclopenthixol; phenothiazines including aliphatic compounds, piperidines and piperazines; thioxanthenes, butyrophenones and substituted benzamides.

24) Antirheumatic agents such as, for example, diclofenac, heparinoid, hydroxychloroquine and methotrexate, leflunomide and teriflunomide.

25) Anxiolytics such as, for example, adinazolam, alpidem, alprazolam, alseroxlon, amphenidone, azacyclonol, bromazepam, bromisovalum, buspirone, captodiamine, capuride, carbcloral, carbromal, chloral betaine, chlordiazepoxide, clobenzepam, enciprazine, flesinoxan, flurazepam, hydroxyzine, ipsapiraone, lesopitron, loprazolam, lorazepam, loxapine, mecloqualone, medetomidine, methaqualone, methprylon, metomidate, midazolam, oxazepam, propanolol, tandospirone, trazadone, zolpidem and zopiclone.

26) Appetite stimulants such as, for example, dronabinol.

27) Appetite suppressants such as, for example, fenfluramine, phentermine and sibutramine; and anti-obesity treatments such as, for example, pancreatic lipase inhibitors, serotonin and norepinephrine re-uptake inhibitors, and anti-anorectic agents.

28) Benzodiazepines such as, for example, alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam.

29) Bisphosphonates such as, for example, alendronate sodium, sodium clodronate, etidronate disodium, ibandronic acid, pamidronate disodium, isedronate sodium, tiludronic acid and zoledronic acid.

30) Blood modifiers such as, for example, cilostazol and dipyridamol, and blood factors.

31) Cardiovascular agents such as, for example, acebutalol, adenosine, amiloride, amiodarone, atenolol, benazepril, bisoprolol, bumetanide, candesartan, captopril, clonidine, diltiazem, disopyramide, dofetilide, doxazosin, enalapril, esmolol, ethacrynic acid, flecanide, furosemide, gemfibrozil, ibutilide, irbesartan, labetolol, losartan, lovastatin, metolazone, metoprolol, mexiletine, nadolol, nifedipine, pindolol, prazosin, procainamide, propafenone, propranolol, quinapril, quinidine, ramipril, sotalol, spironolactone, telmisartan, tocainide, torsemide, triamterene, valsartan and verapamil.

32) Calcium channel blockers such as, for example, amlodipine, bepridil, diltiazem, felodipine, flunarizine, gallopamil, isradipine, lacidipine, lercanidipine, nicardipine, nifedipine, nimodipine and verapamil.

33) Central nervous system stimulants such as, for example, amphetamine, brucine, caffeine, dexfenfluramine, dextroamphetamine, ephedrine, fenfluramine, mazindol, methyphenidate, modafmil, pernoline, phentermine and sibutramine.

34) Cholesterol-lowering drugs such as, for example, acipimox, atorvastatin, ciprofibrate, colestipol, colestyramine, bezafibrate, ezetimibe, fenofibrate, fluvastatin, gemfibrozil, ispaghula, nictotinic acid, omega-3 triglycerides, pravastatin, rosuvastatin and simvastatin.

35) Drugs for cystic fibrosis management such as, for example, *Pseudomonas aeruginosa* infection vaccines (eg Aerugen™), alpha 1-antitripsin, amikacin, cefadroxil, denufosol, duramycin, glutathione, mannitol, and tobramycin.

36) Diagnostic agents such as, for example, adenosine and aminohippuric acid.

37) Dietary supplements such as, for example, melatonin and vitamins including vitamin E.

38) Diuretics such as, for example, amiloride, bendroflumethiazide, bumetanide, chlortalidone, cyclopenthiazide, furosemide, indapamide, metolazone, spironolactone and torasemide.

39) Dopamine agonists such as, for example, amantadine, apomorphine, bromocriptine, cabergoline, lisuride, pergolide, pratnipexole and ropinerole.

40) Drugs for treating erectile dysfunction, such as, for example, apomorphine, apomorphine diacetate, moxisylyte, phentolamine, phosphodiesterase type 5 inhibitors, such as sildenafil, tadalafil, vardenafil and yohimbine.

41) Gastrointestinal agents such as, for example, atropine, hyoscyamine, famotidine, lansoprazole, loperamide, omeprazole and rebeprazole.

42) Hormones and analogues such as, for example, cortisone, epinephrine, estradiol, insulin, Ostabolin-C, parathyroid hormone and testosterone.

43) Hormonal drugs such as, for example, desmopressin, lanreotide, leuprolide, octreotide, pegvisomant, protirelin, salcotonin, somatropin, tetracosactide, thyroxine and vasopressin.

44) Hypoglycaemics such as, for example, sulphonylureas including glibenclamide, gliclazide, glimepiride, glipizide and gliquidone; biguanides including metformin; thiazolidinediones including pioglitazone, rosiglitazone, nateglinide, repaglinide and acarbose.

45) Immunoglobulins.

46) Immunomodulators such as, for example, interferon (e.g. interferon beta-Ia and interferon beta-Ib) and glatiramer.

47) Immunosupressives such as, for example, azathioprine, cyclosporin, mycophenolic acid, rapamycin, sirolimus and tacrolimus.

48) Mast cell stabilizers such as, for example, cromoglycate, iodoxamide, nedocromil, ketotifen, tryptase inhibitors and pemirolast.

49) Drugs for treatment of migraine headaches such as, for example, almotriptan, alperopride, amitriptyline, amoxapine, atenolol, clonidine, codeine, coproxamol, cyproheptadine, dextropropoxypene, dihydroergotamine, diltiazem, doxepin, ergotamine, eletriptan, fluoxetine, frovatriptan, isometheptene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and non-steroidal anti-inflammatory drugs.

50) Drugs for treatment of motion sickness such as, for example, diphenhydramine, promethazine and scopolamine.

51) Mucolytic agents such as N-acetylcysteine, ambroxol, amiloride, dextrans, heparin, desulphated heparin, low molecular weight heparin and recombinant human DNase.

52) Drugs for multiple sclerosis management such as, for example, bencyclane, methylprednisolone, mitoxantrone and prednisolone.

53) Muscle relaxants such as, for example, baclofen, chlorzoxazone, cyclobenzaprine, methocarbamol, orphenadrine, quinine and tizanidine.

54) NMDA receptor antagonists such as, for example, mementine.

55) Nonsteroidal anti-inflammatory agents such as, for example, aceclofenac, acetaminophen, alminoprofen, amfenac, amin-prop-loanm, ixetrine, aspirin, benoxaprofen, bromfenac, bufexamac, carprofen, celecoxib, choline, cinchophen, cinmetacin, clometacin, clopriac, diclofenac, diclofenac sodium, diflunisal, ethenzamide, etodolac, etoricoxib, fenoprofen, flurbiprofen, ibuprofen, indomethacin, indoprofen, ketoprofen, ketorolac, loxoprofen, mazipredone, meclofenamate, mefenamic acid, meloxicam, nabumetone, naproxen, nimesulide, parecoxib, phenylbutazone, piroxicam, pirprofen, rofecoxib, salicylate, sulindac, tiaprofenic acid, tolfenamate, tolmetin and valdecoxib.

56) Nucleic-acid medicines such as, for example, oligonucleotides, decoy nucleotides, antisense nucleotides and other gene-based medicine molecules.

57) Opiates and opioids such as, for example, alfentanil, allylprodine, alphaprodine, anileridine, benzylmorphine, bezitramide; buprenorphine, butorphanol, carbiphene, cipramadol, clonitazene, codeine, codeine phosphate, dextromoramide, dextropropoxyphene, diamorphine, dihydrocodeine, dihydromorphine, diphenoxylate, dipipanone, fentanyl, hydromorphone, L-alpha acetyl methadol, levorphanol, lofentanil, loperamide, meperidine, meptazinol, methadone, metopon, morphine, nalbuphine, nalorphine, oxycodone, papaveretum, pentazocine, pethidine, phenazocine, pholcodeine, remifentanil, sufentanil, tramadol, and combinations thereof with an anti-emetic.

58) Opthalmic preparations such as, for example, betaxolol and ketotifen.

59) Osteoporosis preparations such as, for example, alendronate, estradiol, estropitate, raloxifene and risedronate.

60) Other analgesics such as, for example, apazone, benzpiperylon, benzydamine, caffeine, cannabinoids, clonixin, ethoheptazine, flupirtine, nefopam, orphenadrine, pentazocine, propacetamol and propoxyphene.

61) Other anti-inflammatory agents such as, for example, B-cell inhibitors, p38 MAP kinase inhibitors and TNF inhibitors.

62) Phosphodiesterase inhibitors such as, for example, non-specific phosphodiesterase inhibitors including theophylline, theobromine, IBMX, pentoxifylline and papaverine; phosphodiesterase type 3 inhibitors including bipyridines such as milrinone, amrinone and olprinone; imidazolones such as piroximone and enoximone; imidazolines such as imazodan and 5-methyl-imazodan; imidazo-quinoxalines; and dihydropyridazinones such as indolidan and LY 181 5 12 (5-(6-0~0-1,4,5,6-tetrahydro-pyridazin-3-y~)-I,3-dihydro-indo--2-one); dihydroquinolinone compounds such as cilostamide, cilostazol, and vesnarinone; motapizone; phosphodiesterase type 4 inhibitors such as cilomilast, etazolate, rolipram, oglemilast, roflumilast, ON0 6126, tolafentrine and zardaverine, and including quinazolinediones such as nitraquazone and nitraquazone analogs; xanthine derivatives such as denbufylline and arofylline; tetrahydropyrimidones such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxybenzylamino)-5[N-(2-pyrimidinyl methyl)carbamoyl] pyrimidine, 2-(5,6,7,8-tetrahydro-1,7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxy-benzylamino)-5-[N-(I,3,5-trimethyl-4-pyrazolyl)carbamoyl]-pyrimidine).

63) Potassium channel modulators such as, for example, cromakalim, diazoxide, glibenclamide, levcromakalim, minoxidil, nicorandil and pinacidil.

64) Prostaglandins such as, for example, alprostadil, dinoprostone, epoprostanol and misoprostol.

65) Respiratory agents and agents for the treatment of respiratory diseases including bronchodilators such as, for example, the β2-agonists bambuterol, bitolterol, broxaterol, carmoterol, clenbuterol, fenoterol, formoterol, vilanterol, indacaterol, levalbuterol, metaproterenol, orciprenaline, picumeterol, pirbuterol, procaterol, reproterol, rimiterol, salbutamol, salmeterol, terbutaline and the like; inducible nitric oxide synthase (iNOS) inhibitors; the antimuscarinics ipratropium, ipratropium bromide, oxitropium, tiotropium, glycopyrrolate and the like; the xanthines aminophylline, theophylline and the like; adenosine receptor antagonists, cytokines such as, for example, interleukins and interferons; cytokine antagonists and chemokine antagonists including cytokine synthesis inhibitors, endothelin receptor antagonists, elastase inhibitors, integrin inhibitors, leukotrine receptor antagonists, prostacyclin analogues, and ablukast, ephedrine, epinephrine, fenleuton, iloprost, iralukast, isoetharine, isoproterenol, montelukast, ontazolast, pranlukast, pseudoephedrine, sibenadet, tepoxalin, verlukast, zafirlukast and zileuton.

66) Sedatives and hypnotics such as, for example, alprazolam, butalbital, chlordiazepoxide, diazepam, estazolam, flunitrazepam, flurazepam, lorazepam, midazolam, temazepam, triazolam, zaleplon, zolpidem, and zopiclone.

67) Serotonin agonists such as, for example, 1-(4-bromo-2,5-dimethoxyphenyl)-2-aminopropane, buspirone, m-chlorophenylpiperazine, cisapride, ergot alkaloids, gepirone, 8-hydroxy-(2-N,N-dipropylamino)-tetraline,ip saperone, lysergic acid diethylamide, 2-methyl serotonin, mezacopride, sumatriptan, tiaspirone, trazodone and zacopride.

68) Serotonin antagonists such as, for example, amitryptiline, azatadine, chlorpromazine, clozapine, cyproheptadine, dexfenfluramine, R(+)-a-(2,3-dimethoxyphenyl)-I-[2-(4-fluorophenyl)ethyl]-4-piperidine-methanold, lasetron, fenclonine, fenfluramine, granisetron, ketanserin, methysergide, metoclopramide, mianserin, ondansetron, risperidone, ritanserin, trimethobenzamide and tropisetron.

69) Steroid drugs such as, for example, alcometasone, beclomethasone, beclomethasone dipropionate, betamethasone, budesonide, butixocort, ciclesonide, clobetasol, deflazacort, diflucortolone, desoxymethasone, dexamethasone, fludrocortisone, flunisolide, fluocinolone, fluometholone, fluticasone, fluticasone proprionate, hydrocortisone, methylprednisolone, mometasone, nandrolone decanoate, neom~cin sulphate, prednisolone, rimesolone, rofleponide, triamcinolone and triamcinolone acetonide.

70) Sympathomimetic drugs such as, for example, adrenaline, dexamfetamine, dipirefin, dobutamine, dopamine, dopexamine, isoprenaline, noradrenaline, phenylephrine, pseudoephedrine, tramazoline and xylometazoline.

71) Nitrates such as, for example, glyceryl trinitrate, isosorbide dinitrate and isosorbide mononitrate.

72) Skin and mucous membrane agents such as, for example, bergapten, isotretinoin and methoxsalen.

73) Smoking cessation aids such as, for example, bupropion, nicotine and varenicline.

74) Drugs for treatment of Tourette's syndrome such as, for example, pimozide.

75) Drugs for treatment of urinary tract infections such as, for example, darifenicin, oxybutynin, propantheline bromide and tolteridine.

76) Vaccines.

77) Drugs for treating vertigo such as, for example, betahistine and meclizine.

78) Therapeutic proteins and peptides such as acylated insulin, glucagon, glucagon-like peptides, exendins, insulin, insulin analogues, insulin aspart, insulin detemir, insulin glargine, insulin glulisine, insulin lispro, insulin zinc, isophane insulins, neutral, regular and insoluble insulins, protamine zinc insulin, antibodies and antibody fragments.

79) Anticancer agents such as, for example, anthracyclines, doxorubicin, idarubicin, epirubicin, methotrexate, taxanes, paclitaxel, docetaxel, cisplatin, *vinca* alkaloids, vincris tine and 5-fluorouracil.

80) Pharmaceutically acceptable salts or derivatives of any of the foregoing.

It should be noted that medicaments listed above under a particular indication or class may also find utility in other indications. A plurality of medicaments can be employed in the practice of the present invention. A drug delivery system according to the invention may also be used to deliver combinations of two or more different medicaments.

In one embodiment of the invention the medicament or combination of medicaments are suitable for the treatment of a respiratory disorder. In one embodiment the respiratory disorder is asthma or COPD.

In one embodiment the pharmaceutically active material is selected from a long-acting muscarinic antagonist and/or long-acting beta-adrenoceptor agonist and/or an inhaled corticosteroid.

In one embodiment the medicament is selected from budesonide, formoterol fumarate dihydrate, tiotropium, fluticasone propionate, salmeterol xinafoate, vilanterol trifenatate, umeclidinium bromide, glycopyrronium bromide or indacaterol maleate.

In one embodiment the pharmaceutically active material is glycopyrronium bromide. In one embodiment the pharmaceutically active material is a combination of glycopyrronium bromide and indacaterol maleate.

In one embodiment the medicament is selected from budesonide and formoterol fumarate dehydrate. In one embodiment the medicament is selected from fluticasone propionate and salmeterol xinafoate. In one embodiment the medicament is selected from fluticasone propionate and vilanterol trifenatate. In one embodiment the medicament is selected from umeclidinium bromide and vilanterol trifenatate.

Containers and Inhalation Devices

It is another aim of the present invention to provide a container comprising conditioned taurine or a composition comprising conditioned taurine. Containers which are suitable for use in the present invention include either a bulk storage container, such as a multi-dose reservoir for a dry powder inhaler, or unit dose containers such as a capsule or a blister. The capsule may be formed from various materials e.g. gelatine, cellulose derivatives such as hydroxypropyl methylcellulose (HPMC) or hydroxypropylcellulose (HPC), starch, starch derivatives, chitosan or synthetic plastics, while the blister may be provided in the form of a blister pack or blister strip.

Containers which are also considered suitable for use in the present invention include pMDI canisters.

Administration

In a further aspect of the present invention, the conditioned taurine or a composition comprising conditioned taurine, suitable for inhalation, are preferably administered via a dry powder inhaler (DPI). In a dry powder inhaler, the dose to be administered is stored in the form of a non-pressurized dry powder and, on actuation of the inhaler the particles of the powder are expelled from the device in the form of a cloud of finely dispersed particles that may be inhaled by the patient.

Dry powder inhalers can be "passive" devices in which the patient's breath is the only source of gas which provides a motive force in the device. Examples of "passive" dry powder inhaler devices include the Rotahaler™ and Discus/Diskhaler™, the Monohaler™, the GyroHaler™ Turbuhaler™ and Novolizer™. Alternatively, "active" devices may be used, in which a source of compressed gas or alternative energy source is used. Examples of suitable active devices include Aspirair™ and the active inhaler device produced by Nektar Therapeutics (as covered by U.S. Pat. No. 6,257,233).

It is generally considered that different compositions perform differently when dispensed using passive and active type inhalers. Passive devices create less turbulence within the device and the powder particles are moving more slowly when they leave the device. This leads to some of the metered dose remaining in the device and, depending on the nature of the composition, less de-agglomeration upon actuation. However, when the slow moving cloud is inhaled, less deposition in the throat is often observed. In contrast, active devices create more turbulence when they are activated. This results in more of the metered dose being extracted from the blister or capsule and better de-agglomeration as the powder is subjected to greater shear forces. However, the particles leave the device moving faster than with passive devices and this can lead to an increase in throat deposition.

Particular "passive" dry powder inhalers that may be mentioned herein are "passive" dry powder inhalation devices that are described in WO 2010/086285. Particularly, "active" dry powder inhalers that may be mentioned herein are referred to as Aspirair® inhalers and are described in more detail in WO 2001/00262, WO 2002/07805, WO 2002/89880 and WO 2002/89881. It should be appreciated, however, that conditioned taurine or a composition comprising conditioned taurine of the present invention can be administered with either passive or active inhaler devices.

In another aspect of the present invention, the conditioned taurine or a composition comprising conditioned taurine, suitable for inhalation, are preferably administered via a spray or aerosol device, such as a pressurised metered dose inhaler (pMDI). The composition (whether in solution or suspension) may be for pulmonary, nasal, buccal or topical administration, but preferably for pulmonary inhalation.

The pMDI is dependent upon the propulsive force of a propellant system used in its manufacture to dispense the composition from the device in a form that may be inhaled by a patient. The propellant generally comprises a mixture of liquefied hydrofluorocarbons (HFAs) which are selected to provide the desired vapour pressure and stability of the formulation. Propellants HFA 227 (1,1,1,2,3,3,3-heptafluoropropane) and HFA 134a (1,1,1,2-tetrafluoroethane) or mixtures thereof are currently the most widely used propellants in aerosol formulations for inhalation administration.

Additional embodiments of the invention include the following:

Conditioned taurine suitable for inhalation. Conditioned taurine which is crystalline.

Conditioned taurine as an inhalation excipient.

A pharmaceutical composition comprising conditioned taurine.

A pharmaceutical composition comprising conditioned taurine further comprising an amino acid. The amino acid may be selected from the group consisting of alanine, leucine, isoleucine, lysine, valine, methionine or phenylalanine, in one embodiment leucine. The leucine may be present in an amount less than 10%, less than 9%, less than 8%, less than 7%, less than 6%, less than 5%, less than 4%, less 3%, less than 2%, less than 1% by weight based on the dry weight of the composition.

A pharmaceutical composition comprising conditioned taurine further comprising a medicament or combinations of medicaments.

A pharmaceutical composition of the invention wherein the taurine and at least one other component are co-spray-dried using the spray drying conditions effective to produce conditioned taurine.

A pharmaceutical composition of the invention suitable for inhalation.

A pharmaceutical composition of the invention wherein the conditioned taurine acts as an excipient, carrier or diluent.

A pharmaceutical composition of the invention where the amino acid is located on the surface of the conditioned taurine.

Conditioned taurine made by a spray-drying method comprising:

(a) providing a feedstock comprising raw taurine in an aqueous solution or suspension; and
(b) spray-drying the feedstock under conditions to create particles that demonstrate no significant net change in the $D_{90}$ (±20%) after 7 days of ambient storage and have a particle size ($D_{90}$) of <20 μm, but more preferably <10 μm after 7 days of ambient storage.

A further embodiment of the invention is a method for preparing conditioned taurine comprising:

(a) providing a feedstock comprising raw taurine in an aqueous solution or suspension; and
(b) spray-drying the feedstock under conditions to create particles that demonstrate no significant net change in the $D_{90}$ (±20%) after 7 days of ambient storage and have a particle size ($D_{90}$) of <20 μm, but more preferably <10 μm after 7 days of ambient storage.

A further embodiment is a method of the invention wherein the pH of the feedstock is between pH 1 and pH 7, in one embodiment between pH 3 and pH 5.

A further embodiment is a method of the invention wherein the pH of the feedstock is acidic e.g. less than pH 5, in one embodiment equal to or less than pH4, such as about pH4.

A further embodiment is a method of the invention wherein the feedstock concentration of taurine is between 0.1% and 10%, in one embodiment between 1% and 5%.

A further embodiment is a method of the invention wherein the feedstock concentration of taurine is less than 5%, such as less than 4%, such as less than 3%, such as less than 2%, such as about 1%.

A further embodiment is a method of the invention wherein the feedstock temperature is between 0.1° C. and 100° C., in one embodiment between 20° C. and 70° C.

A further embodiment is a method of the invention wherein the feedstock temperature is less than 70° C., such as less than 60° C., such as less than 50° C., such as less than 40° C. such as less than 30° C.

A further embodiment is a method of the invention wherein the outlet temperature of the spray drying apparatus is between 50° C. and 120° C., in one embodiment between 60° C. and 100° C.

A further embodiment is a method of the invention wherein the outlet temperature is less than 100° C., in one embodiment less than 90° C., in one embodiment less than 80° C., still in one embodiment less than 70° C., such as about 60° C.

A further embodiment is a method of the invention wherein the $T_{(solid:gas)}$ ratio is between $2.00\times10^{-6}$ and $2.75\times10^{-3}$.

A further embodiment is a method of the invention for preparing conditioned taurine wherein the conditioned taurine particles have a particle size ($D_{90}$) that remain below 20 μm after 7 days of ambient storage post spray drying.

A further embodiment is a method of the invention used to make a composition comprising taurine which further comprises an amino acid, e.g. selected from the group consisting of alanine, leucine, isoleucine, lysine, valine, methionine or phenylalanine, in one embodiment leucine.

A further embodiment is a method of the invention used to make a composition comprising taurine which further comprises a medicament or combinations of medicaments.

A further embodiment is a container comprising:

(a) conditioned taurine; or (b) a composition comprising conditioned taurine

The container may be a reservoir for a dry powder inhaler, a blister or a capsule. In one embodiment the container is a blister such as a foil blister.

Conditioned taurine having a moisture content of less than 2% by weight, optionally less than 1% by weight, optionally less than 0.5% by weight of conditioned taurine.

Optionally the composition further comprises leucine and a medicament or combinations of medicaments. The composition may be a powder.

EXAMPLES

The following examples are provided to illustrate the invention but should not be construed as limiting the invention.

Example 1—Experimental Spray Drying Strategy

Figure 7:
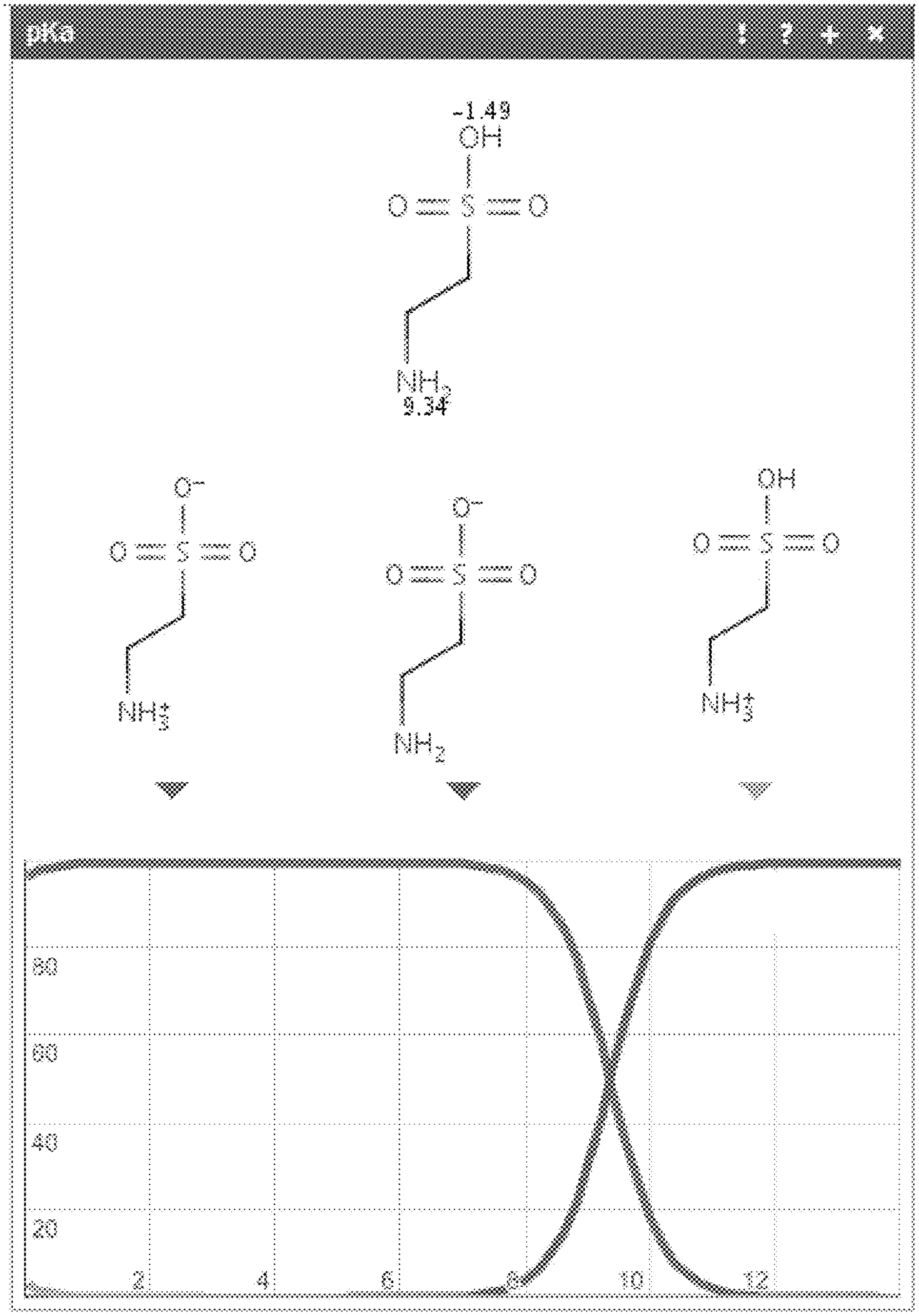
FIG. 7 depicts the pKa profile of taurine.

Zwitterionic Hypothesis:

As taurine is a zwitterionic compound, it is believed that the sulphur-hydyl group of the taurine becomes ionised (oxidation) with the proton being added to the amine group (reduction), in the feedstock and retains a charge even after drying. This leads to the material relaxing on storage which is believed to be the charged groups neutralising resulting in a conformatorial structural change. This conformatorial change causes agglomeration of the particles in the dry state, leading to a significant reduction in the aerosol performance. It is believed the neutralisation has a vitrification intermediate phase, which is the cause of the agglomeration (See FIG. 7).

Materials:

Raw taurine was obtained from Sigma-Aldrich Chemicals (The old brickyard, New road, Gillingham, Dorset, SP8 4XT). Sodium Hydroxide, hydrochloric acid and citric acid were obtained from Fisher Scientific (Bishop Meadow Road, Loughborough, LE11 5RG).

Spray Drying Strategy:

The Taurine spray drying process was investigated by producing 24 batches with varying process and formulation parameters (factors). These were:

Drying Gas flow rate
Atomisation gas flow rate
Feedstock pumping rate
Outlet temperature
Feedstock temperature
Feedstock concentration
Feedstock pH and buffer/acid type These process and formulation parameters (factors) examined also affect the zwitterionic neutralisation process and the hypothesis behind them are discussed below. The values for the extremes and centre points (levels) for each of the factors were determined on well documented physical design limits for spray dryers.

Drying Gas Flow Rate Parameters and Rationale:

a) Definition of the Operation Range

The drying gas flow rates range were determined as being just high enough to maintain particles in the airstream during drying while allowing a particle to have sufficient residence time in the drying chamber to complete drying. A significant enough velocity is required to maintain curvilinear flow through the equipment and prevent premature deposition of the particles in the drying chamber of transfer conduit before collection and classification in the cyclone. If the drying gas is too high, then the velocity of the particles will be too high to have sufficient time in the drying gas for complete evaporation of all of the water from the feedstock to occur, resulting in high residual moisture (often >5.0% w/w). If particles have high residual moisture, then they are liable to agglomerate strongly through capillary forces and if partial dissolution occurs, then solid bridging will occur. For this investigation and for the VSD equipment, the lower limit is defined as 12.0 $Kg\cdot Hr^{-1}$ and the upper limit defined as 15.0 $Kg\cdot Hr^{-1}$ and the centre point was defined as 13.5 $Kg\cdot Hr^{-1}$.

b) Impact and Effect on the Zwitterionic Neutralisation

The drying gas is believed to affect the neutralisation process of the taurine's sulphur-hydryl group, impacting the physical stability. A lower drying gas flow, results in a lower drying gas velocity, which in turn lowers the velocity of droplets and resultant particles. The lower velocity causes a slower rate of evaporation and results in a longer time period for charge neutralisation, giving particles more stable form, preventing the storage agglomeration that has been observed.

Atomisation Gas Flow Rate Parameters and Rationale:

a) Definition of the Operation Range

The atomisation gas flow rate range was chosen to reflect the lowest limit where particles of inhalation size range for a given nozzle are produced. The upper limit defined as giving dry particles and no significant decrease in the $D_{50}$ of the resultant particles, at a given drying gas flow rate. At higher atomisation flow rates, droplets/particles possess too high velocity and therefore low residence time in the drying chamber, resulting in particles with high residual moisture (often >5.0% w/w). If particles have high residual moisture, then they are liable to agglomeration. In extreme case, too high atomisation gas causes collisions between droplets before complete drying, leading to agglomerates being formed. For this investigation and for the VSD equipment, the lower limit is defined as 12.0 $L\cdot min^{-1}$ and the upper limit defined as 18.0 $L\cdot min^{-1}$, the centre point was defined as 15.0 $L\cdot min^{-1}$.

b) Impact and Effect on the Zwitterionic Neutralisation

The atomisation gas flow rate has been shown to have an impact on the physical stability of spray dried taurine. One theory attributed to this mechanism is that there is a high degree of interaction of the atomising gas, with the liquid, not just to form small and uniform droplets, but to catalyse the neutralisation of the zwitterionic charges, potentially through oxidation of the sulphur-hydryl group of taurine.

Feedstock Pumping Rate Parameters and Rationale:

a) Definition of the Operation Range

The feedstock pumping rates range was chosen to reflect the lowest limit where the production rate of product was high enough to obtain sufficient material for analysis in a reasonable amount of time. While lower rates can be achieved, too low a feedrate would take an unreasonable amount of time to produce a batch and would have commercial limitations. The upper level was defined as the feedrate at which, for a given drying and atomisation gas flow rate, the particles produced were not effectively dried due to oversaturation of the drying gas resulting in particles with high residual moisture (often >5.0% w/w). If particles have high residual moisture, then they are liable to agglomeration. For this investigation and for the VSD equipment, the lower limit is defined as 1.5 $mL \cdot min^{-1}$ and the upper limit defined as 4.5 $mL \cdot min^{-1}$, the centre point was defined as 3.0 $mL \cdot min^{-1}$.

b) Impact and Effect on the Zwitterionic Neutralisation

The feed rate controls the amount of feedstock in the drying chamber per unit time. Therefore, the feed rate has a direct effect on the drying capacity of the gas through altering the saturation concentration of water, which in turn alters the drying kinetics of the system and resultant particles. A low feed rate would have a larger drying capacity margin for the drying gas resulting in faster drying and thus potentially leading to less physically stable particles.

Outlet Temperature Parameters and Rationale:

a) Definition of the operation Range

The outlet temperature range was chosen to reflect the lowest temperature at which dry particles (often <5.0% w/w moisture) are collected (for the centre-point values of feedstock flow rate, atomisation gas and drying gas flow rates). The upper temperature was defined as the boiling point of water, above which the kinetic rate of evaporation only slightly increases. For this investigation and for the VSD equipment, the lower limit is defined as 60° C. and the upper limit defined as 100° C., the centre point was defined as 80° C.

b) Impact and Effect on the Zwitterionic Neutralisation

The outlet temperature defines the thermal gradient across the drying chamber and thus has a subsequent impact on the drying rate. As discussed for the drying gas rationale, a longer time to evaporate the water and form a particle results in a longer time to allow charge neutrality and the conformatorial change to occur.

Feed stock Temperature Parameters and Rationale:

a) Definition of the Operation Range

The feedstock temperature range was determined as being as low as room temperature, essentially 20° C., with the highest temperature where vapour was being produced resulting in variable concentrations of the feedstock being established throughout the run. With this in mind, 70° C. was chosen.

b) Impact and Effect on the Zwitterionic Neutralisation

The temperature of the feedstock during spray drying will also be investigated to access how the temperature affects the pKa of the sulphur-hydryl group. Theoretically, an increase in the temperature could increase the pKa of the sulphur-hydryl group from the current relatively low 1.49 (henderson-hasselbalch (1908)). This would mean that less acidification and shorter drying times could be required to achieve the same level of physical stability at lower temperatures. In addition, adding heat to the feedstock increases the thermal energy in the atomised droplet which leads to a smaller thermal gradient and may increase the droplet drying kinetics to allow a particle to be dried quicker. As discussed in previous sections, it is hypothesised that the increased drying rate leads to a shorter time for charge neutralisation and thus physical instability on storage.

Feedstock Concentration Parameters and Rationale:

a) Definition of the Operation Range

The feedstock concentration range was chosen as it will affect the drying kinetics and resultant size/density of the produced particles. A minimum of 1.0% w/v is often used to give an efficient production rate, while having acceptable PSD span. Above 5.0% w/v, the particle size increases above the inhalation size range for most 2 fluid nozzles. Therefore, the lower concentration was defined as 1.0% w/v and the upper range defined as 5.0% w/v. The centre point was defined as 2.5% w/v.

b) Impact and Effect on the Zwitterionic Neutralisation

The concentration of the feedstock could have several impacts on the drying kinetics and resultant particle stability. As taurine's sulphur-hydryl group is a strong acid, increasing the concentration of taurine would mean a reduction in the pH. At a certain concentration, the taurine would generate sufficient protons to establish itself at its isoelectric point. This is not so simple if one considers a drying droplet, which alters the concentration as water is lost. Therefore, the initial pH might not necessarily be the optimum.

Feedstock Solution pH and Buffer/Acid Type Parameters and Rationale

Figure 8:
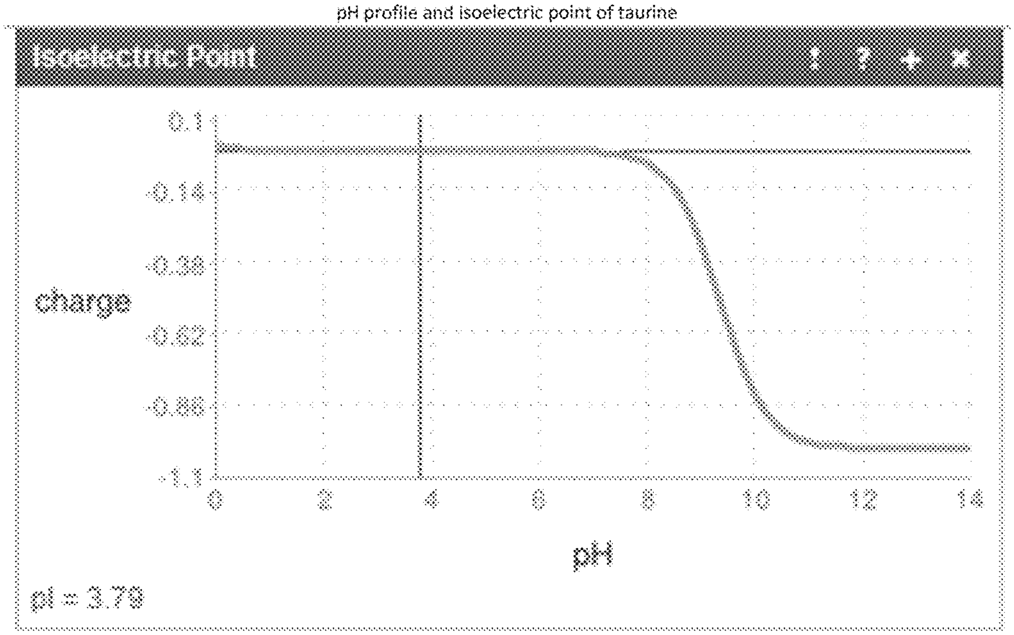
FIG. 8 depicts the pH profile and isoelectric point of taurine.

The pH of the feedstock and the acid used to modify the pH is believed to affect the taurine stability via the zwitterionic theory and driving the molecule to the isoelectric point when in the feedstock solution. Acidifying the solution should allow the taurine to neutralise the sulphur-hydryl groups charge by reaching the molecules isoelectric point, which is calculated to be at pH 4.0 (See FIG. 8). The type of acid to do this may be important too. If the acid boils at too a low a boiling point, or is an azeotrope, the conjugate base and associated proton will be removed in the drying process before the particle is dried and charge neutralisation capability will be lost. But the acid and thus its residual conjugate base must be pharmaceutically acceptable as a salt forming agent, have a strong enough dissociation constant (pKa) to require very small effective concentrations to be effective and a high melting/boiling point to not be lost during drying prematurely.

Therefore, although the values for limits and operation space defined in this investigation are specific to the VSD spray dryer, the experimental strategy can be said to cover the complete operation space for spray drying that can be translated and transposed onto any spray dryer model at any scale where these physical limits and constraints exist.

Batch Preparation:

24 raw taurine samples were dissolved in an appropriate amount of Milli-Q water and sonicated. The pH of each sample was adjusted accordingly. The prepared feedstock solutions were separately spray-dried using a VSD spray-drier with a 0.5 mm, two-fluid nozzle using various combinations of the process and formulation parameters summarised in Table 1.

TABLE 1 summaries the various combinations of the process and formulation parameters analysed

| Batch | Drying Gas | Outlet Temperature | Feed Rate | Feedstock Temperature | Feedstock Concentration | Buffer | pH | Atomisation Flow Rate |
|---|---|---|---|---|---|---|---|---|
| 1 | 15 | 100 | 4.5 | 70 | 1 | Citrate | 4.0 | 15 |
| 2 | 13.5 | 80 | 4.5 | 70 | 1 | N/A | 5.5 | 12 |
| 3 | 13.5 | 100 | 1.5 | 45 | 2.5 | N/A | 5.5 | 15 |
| 4 | 15 | 100 | 3 | 20 | 1 | N/A | 5.5 | 12 |
| 5 | 12 | 80 | 3 | 20 | 1 | HCl | 4.0 | 18 |
| 6 | 12 | 100 | 3 | 45 | 5 | Citrate | 4.0 | 12 |
| 7 | 13.5 | 60 | 1.5 | 45 | 1 | NaOH | 7.0 | 18 |
| 8 | 15 | 60 | 3 | 70 | 2.5 | NaOH | 7.0 | 12 |
| 9 | 13.5 | 60 | 4.5 | 20 | 2.5 | Citrate | 4.0 | 18 |
| 10 | 13.5 | 80 | 3 | 70 | 5 | Citrate | 4.0 | 18 |
| 11 | 15 | 100 | 4.5 | 45 | 5 | HCl | 4.0 | 18 |
| 12 | 12 | 60 | 3 | 45 | 2.5 | N/A | 5.5 | 18 |
| 13 | 15 | 80 | 3 | 20 | 5 | NaOH | 7.0 | 15 |
| 14 | 13.5 | 100 | 3 | 70 | 2.5 | HCl | 4.0 | 15 |
| 15 | 12 | 60 | 1.5 | 70 | 1 | HCl | 4.0 | 12 |
| 16 | 15 | 80 | 4.5 | 45 | 2.5 | HCl | 4.0 | 12 |
| 17 | 12 | 60 | 4.5 | 70 | 5 | N/A | 5.5 | 15 |
| 18 | 15 | 60 | 1.5 | 45 | 1 | Citrate | 4.0 | 15 |
| 19 | 13.5 | 60 | 1.5 | 20 | 5 | HCl | 4.0 | 15 |
| 20 | 12 | 80 | 1.5 | 20 | 2.5 | Citrate | 4.0 | 12 |
| 21 | 12 | 80 | 4.5 | 45 | 1 | NaOH | 7.0 | 15 |
| 22 | 13.5 | 100 | 4.5 | 20 | 5 | NaOH | 7.0 | 12 |
| 23 | 15 | 80 | 1.5 | 70 | 5 | N/A | 5.5 | 18 |
| 24 | 12 | 100 | 1.5 | 70 | 2.5 | NaOH | 7.0 | 18 |

(i) Particle Size Distribution Analysis:

Particle size distributions of the 24 sample batches were measured by laser diffraction using a Sympatec HELOS and RODOS particle size analyser and ASPIROS dispersion unit (0.5 bar dispersion). A focal length corresponding to R4 lens was used and each batch sample was run in triplicate in order to determine the average particle size. In this instance, the $D_{90}$ for each batch sample was derived from the diffraction data using in-built Sympatec software (WINDOX 5.0).

Out of the 24 sample batches analysed, only 8 sample batches (Table 2) were identified as forming conditioned taurine and demonstrated a particle size distribution of $D_{90}<10.0$ μm.

TABLE 2 summarises the PSD ($D_{90}$) R4 lens at T = 0 and T = 7 days

| Sample | PSD R4 $D_{90}$ Mean (μm) T = 0 | PSD P4 $D_{90}$ Mean (μm) T = 7 days |
|---|---|---|
| 11 | 7.42 | 8.90 |
| 13 | 8.30 | 8.79 |
| 15 | 4.82 | 5.80 |
| 16 | 8.19 | 8.44 |
| 17 | 7.89 | 8.17 |
| 19 | 7.86 | 7.91 |
| 20 | 6.51 | 7.34 |
| 23 | 6.62 | 6.89 |

Table 2, highlights the change in the $D_{90}$ using the R4 lens, from initial (T=0) to the 7 day time point (T=7 days). All 8 samples show a small increase (±20%) in the $D_{90}$ between the initial and 7 day time point and consequently the absence of any agglomeration.

Figure 1:
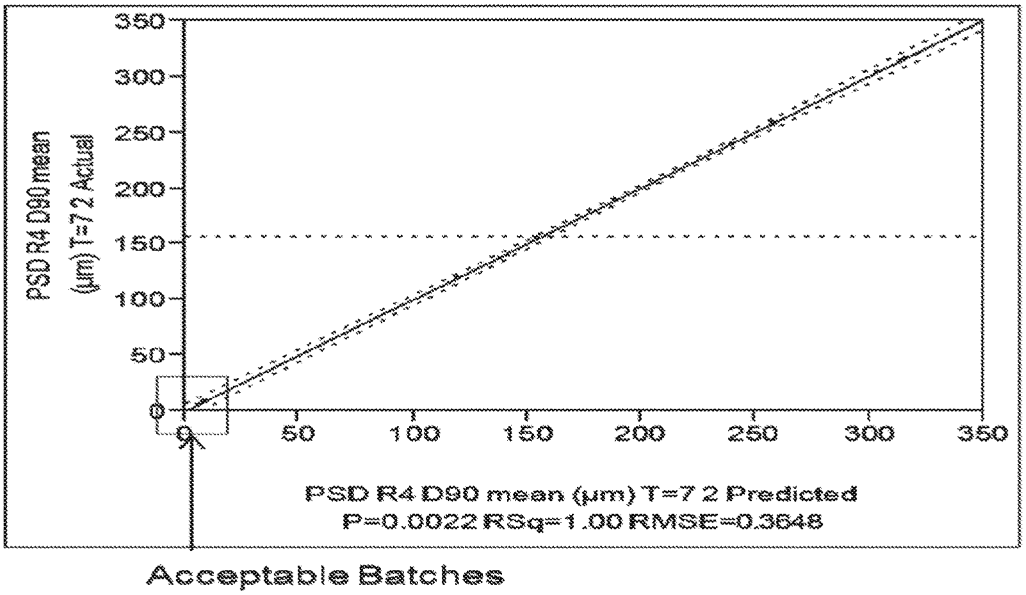
FIG. 1 is a response plot of modelled residual results versus actual data. The boxed area highlights the 8 conditioned taurine batches.

FIG. 1, which depicts a model response plot for all 24 sample batches produced, similarly demonstrates that only 8 have an acceptable PSD profile after 7 days of storage. Statistical analysis reveals that the model was highly significant with an $R^2=1.00$ and significant P value of $p<0.05$, meaning the null hypothesis is rejected and that the parameters modelled are significantly affecting the agglomeration potential of the taurine. The parameters that govern the production of conditioned taurine are feedstock concentration, feedstock pumping rate, drying gas flow rate and second/third order interactions between them.

The joint factor tests indicate from the p-values calculated (see FIG. 9), that all the factors tested are significant.

Taurine can be produced in a form for inhalation that meets the particle size criteria and particle size stability provided the spray drying process is carefully controlled. The control of the parameters is used to allow zwitterionic neutralisation during drying, to prevent this occurring during storage resulting in agglomeration and loss of primary particles. The data verifies the hypothesis that zwitterionic neutralisation is the most likely mechanism responsible for agglomeration in the solid state and that all of the process and formulation parameters tested in this investigation have an impact on this process.

While the model and analysis are specific to the VSD, the full operation space of the dryers capability has been mapped. Therefore, it can be inferred that inhalation taurine produced on any spray dryer and at any scale will exhibit the same dependence on all the parameters and leverages, which control the neutralisation of the zwitterionic charge. It would be straightforward, for any person skilled in the art to map the operation space of a spray dryer and achieve a similar model, with the same level of interdependence of the factors on the production of conditioned taurine.

(ii) Calculating the Ratio of Taurine Dried Per Unit Time During Spray Drying

It has been determined that the inter-relationship between these parameters (feedstock concentration, feedstock pumping rate and drying gas flow rate) can be explained using the following expression, which calculates the amount of taurine being dried versus the amount of drying gas present, per unit time.

$$T_{Solid:\ Gas}=\frac{(C_F\times R_F)}{V_{DG}}$$

Where:

$T_{solid:Gas}$=Mass of taurine per volume of drying gas per unit time (AU)

$C_F$=Feedstock Concentration (g $mL^{-1}$)

$R_F$=Feedrate (mL $min^{-1}$)

$V_{DG}$=Volume of Drying Gas (g $min^{-1}$)

It has been determined by experiment that processed taurine and conditioned taurine products can be produced by spray drying when the $T_{(solid:gas)}$ ratios are between $2.000\times10^{-6}$ (smallest ratio) and $2.750\times10^{-3}$ (largest ratio). The use of a more acidic feedstock is also a significant factor (though not essential) and allows a wider operation window of parameters to be used in the production of conditioned taurine.

Furthermore, to demonstrate that the calculated ratios are applicable to any open loop spray dryer, extrapolations to the Niro spray dryer are shown as exemplification:

Smallest ratio=$3.529\times10^{-6}$

Largest ratio=$2.118\times10^{-3}$

These calculated ratios fall within the range of the VSD spray dryer ratios.

Figure 2:
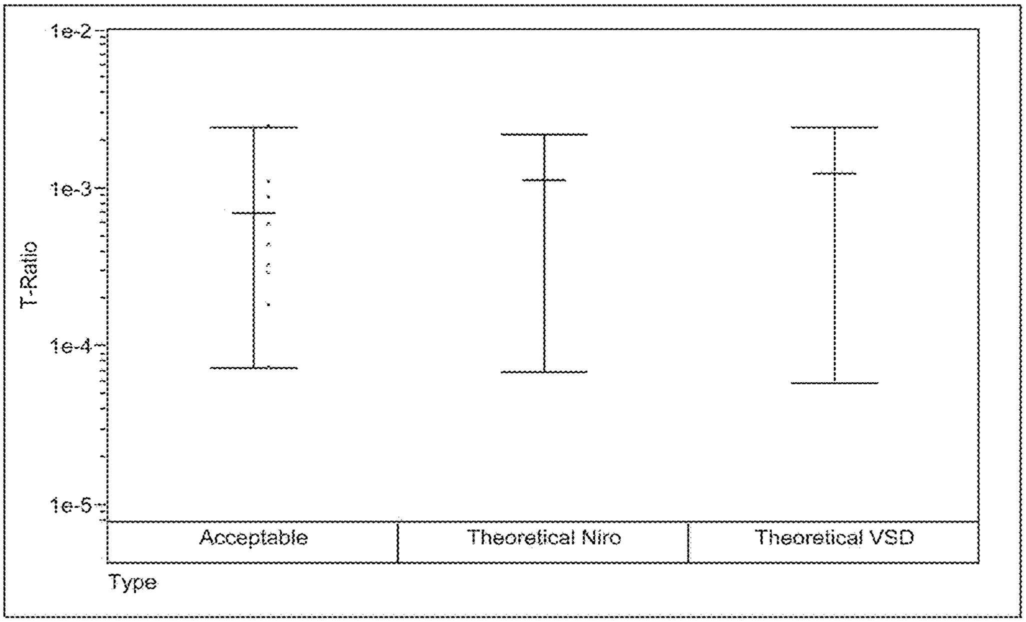
FIG. 2 is a variability chart showing how the 8 conditioned taurine batches span the whole theoretical operating range for spray dryers. The conditioned taurine batches are shown as a function of the $T_{(solid:gas)}$ ratios.

FIG. 2 depicts a visual variability chart showing the spread of the acceptable batches (i.e. conditioned taurine) produced as a function of the $T_{solid:Gas}$ ratios and indicates the relatively even spread across the theoretically operation range for the VSD spray dryer. Furthermore, the theoretical Niro spray dryer parameters are also seen to fall within the VSD operational range.

Figure 3:
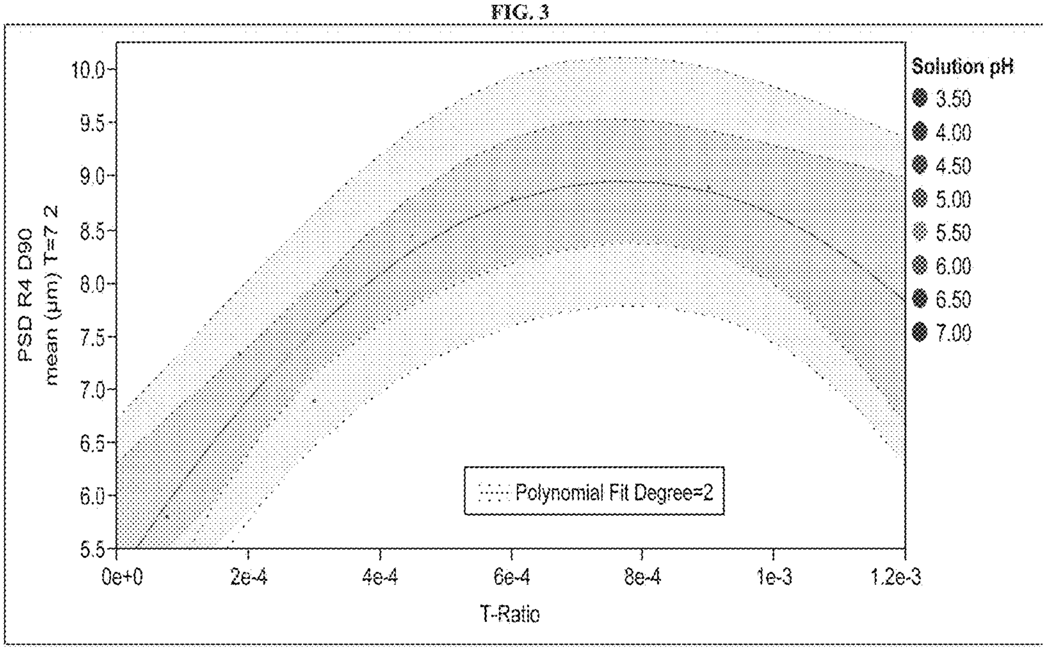
FIG. 3 is a plot showing the relationship of conditioned taurine batches which obey a quadratic relationship with the $D_{90}$ of the PSD after 7 days ($R^2$=0.91 Prob>F 0.0031).

FIG. 3 demonstrates the strong relationship of the conditioned taurine batches which obeys a quadratic relationship with the $D_{90}$ of the PSD after 7 days. Therefore, a batch of any inhalable PSD that is stable i.e. conditioned can be made on any spray dryer at any scale using the quadratic equation defined below. Rearranging the equation will give an appropriate t-ratio which can then be used to select the appropriate drying gas, feed rate and concentration for that dryer based on its functional operation parameter ranges.

$$D_{90}\ (\mu m)=A+BX-CX^2$$

Where:

X=T-Ratio

A=6.8

B=3450.4

C=6230437.9

(iii) Thermogravimetric Analysis:

Thermogravimetric analysis (TGA) determines the changes in sample weight in relation to change in temperature. This technique is used to examine the weight loss due to the removal of water upon heating and gives an assessment of the moisture content of the spray dried taurine samples.

TABLE 3

| summarises the equipment and method used | |
|---|---|
| Equipment | Perkin Elmer TGA 5000 |
| Starting Temperature | 25° C. |
| End Temperature | 200° C. |
| Heating Rate | 10° C./$min^{-1}$ |

Figure 4:
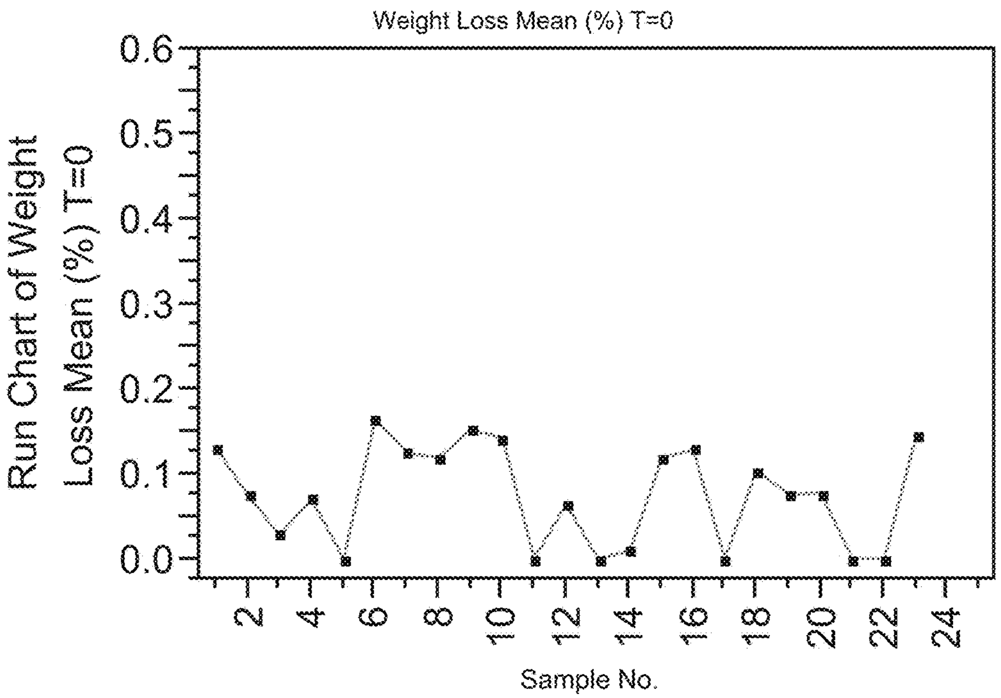
FIG. 4 is a TGA (thermo-gravimetric analysis) graph depicting the weight loss mean as a percentage at the initial time point, T=0 for 24 samples of spray-dried taurine.

FIG. 4 illustrates the moisture content for each sample at the initial time point, T=0. All samples were below 0.2% w/w moisture.

Figure 5:
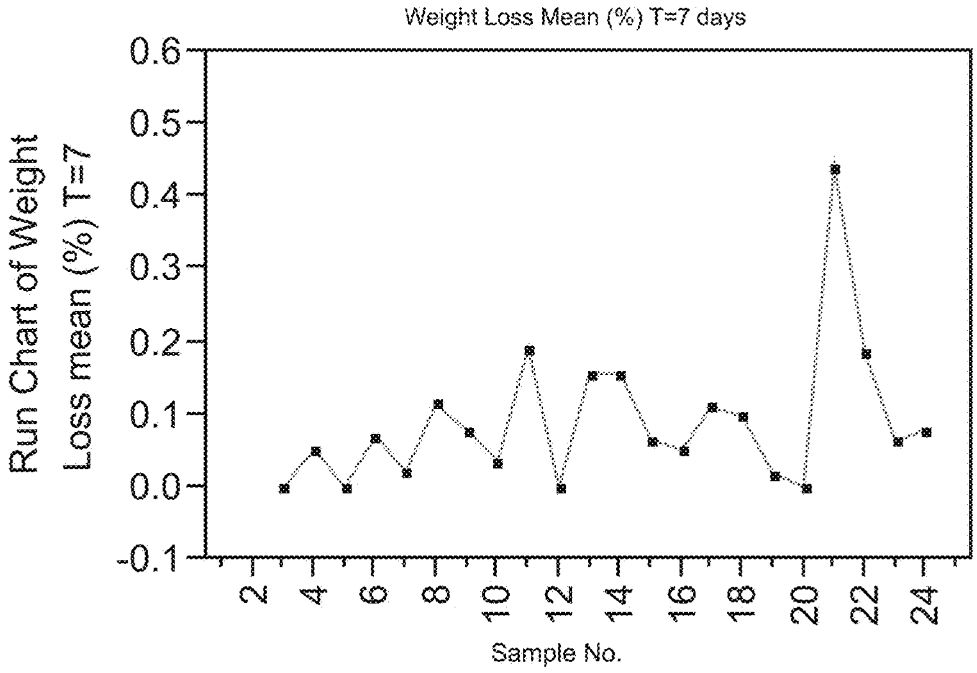
FIG. 5 is a TGA (thermo-gravimetric analysis) graph depicting the weight loss mean as a percentage at the 7 day time point, T=7 days for 24 samples of spray-dried taurine.

FIG. 5 illustrates the moisture content for each sample at the 7 day time point, T=7. All samples were below 0.2% w/w moisture, with the exception of sample batch 21 which measured 0.45% w/w moisture. In some instances the results obtained gave a negative weight loss. This was attributed to the balance drift in conjunction with the very small weight loss experienced and these results were subsequently reported as a zero-weight loss.

Spray drying raw taurine, irrespective of the spray drying conditions used, resulted in spray-dried taurine demonstrating very low moisture content (0.2% w/w in comparison to spray-dried trehalose, which is typically between 3% and 5% w/w). Furthermore, there was no significant change in moisture content during storage.

(iv) Differential Scanning calorimetry

Differential Scanning calorimetry (DSC) is a thermo-analysis technique in which the difference in the amount of heat required to increase the temperature of a sample and reference is measured as a function of temperature. This technique is used to assess the glass Transition temperatures (Tg) and melting characteristics of the spray-dried samples.

Figure 6:
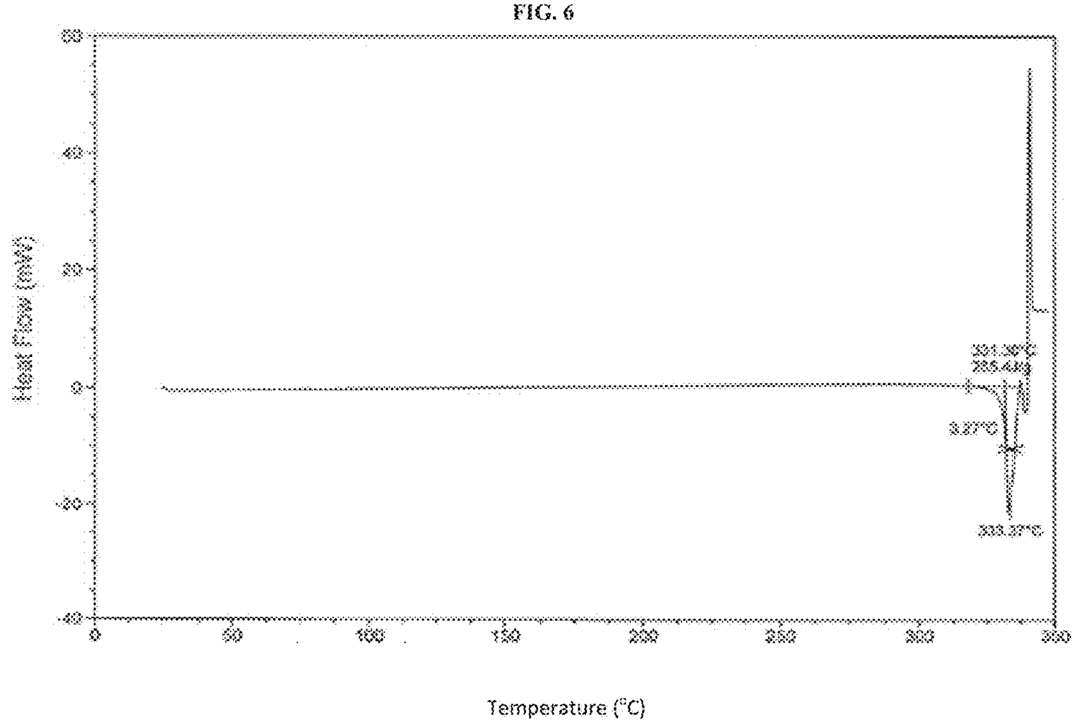
FIG. 6 is a DSC (differential scanning calorimetry) graph depicting a sample of spray-dried taurine.

FIG. 6 illustrates a DSC graph depicting spray-dried taurine, exemplified with sample 2 data.

A glass transition temperature was not observed for any of the samples analysed, indicating that, irrespective of the spray drying conditions used, a transition from an amorphous form to crystalline does not occur, therefore the samples are produced in the crystalline form. The majority of samples examined demonstrated a melting point at approximately 333° C., with the lowest observed melting point seen at approximately 325° C.

Example 2

Materials:

Raw taurine and L-Leucine were obtained from Sigma-Aldrich Chemicals (The old brickyard, New road, Gillingham, Dorset, SP8 4XT). Trehalose was obtained from Ferro Pfanstiehl and Salbutamol sulphate was obtained from Cambrex Pharmaco.

Preparation of Salbutamol Sulphate/Taurine OR Trehalose/L-Leucine Samples:

Salbutamol sulphate (1% w/w), raw taurine OR trehalose (98.5% w/w) and L-Leucine (0.5% w/w) samples were dissolved in Milli-Q-water (800 ml) and sonicated. The prepared feedstock solutions were separately spray-dried using the Niro Mobile Minor X3000 with a 0.5 mm, two-fluid nozzle, according to the parameters outlined below in Table 4 and 5:

TABLE 4

Summarises the PSD R4 lens at T = 0 and T = 24

| Sample | Parameters | Storage | Time Point | PSD $D_{10}$ | PSD $D_{50}$ | PSD $D_{90}$ |
|---|---|---|---|---|---|---|
| Tre/Leu/Sal | Process | | 0 | 0.73 | 1.65 | 3.44 |
| | A | Ambient | 24 h | 0.82 | 2.27 | 245.71 |
| | | 25° C./50% RH | 24 h | NA | NA | NA |
| Tau/Leu/Sal | Process | | 0 | 0.75 | 1.75 | 3.86 |
| | B | Ambient | 24 h | 0.75 | 1.74 | 3.80 |
| | | 25° C./50% RH | 24 h | 0.76 | 1.79 | 4.03 |
| Tre/Leu/Sal | Process | | 0 | 0.72 | 1.59 | 3.20 |
| | B | Ambient | 24 h | 0.94 | 75.80 | 279.99 |
| | | 25° C./50% RH | 24 h | NA | NA | NA |

Process A is a spray drying process using appropriate spray drying conditions specific to the Niro Mobile Minor X3000 for producing optimal trehalose particles suitable for inhalation. It should be noted that these conditions can be modified by a person skilled in the art to ensure that trehalose particles suitable for inhalation are produced regardless of the spray drying machine used.

Process B is a spray drying process using appropriate spray drying conditions specific to the Niro Mobile Minor X3000 for producing optimal taurine particles, namely conditioned taurine, suitable for inhalation. These conditions can also be modified depending on the spray drying machine used.

TABLE 5 summarises the spray drying parameters for Process A and Process B

| Component | Process Parameters | Conditions Used: Process A | Process B |
|---|---|---|---|
| Drying Gas | Pressure | 30 +/− 5.0 mm $Wg^{-1}$ | |
| | Outlet Temperature | 90.0° C. +/− 3.0° C. | 60.0° C. +/− 3.0° C. |
| | Inlet Temperature | 160.0° C. +/− 3.0° C. | 120.0° C. +/− 3.0° C. |
| Feedstock | Temperature | 20.0° C. +/− 5.0° C. | 50.0° C. +/− 5.0° C. |
| | Concentration | 2.5% w/v | |
| Atomisation Gas | Flow Rate | 150 +/− 10 L $min^{-1}$ | 200 +/− 10 L $min^{-1}$ |
| | Pressure | 1.6 +/− 0.2 bar | 3.9 +/− 0.2 bar |

Table 4 demonstrates that storage of Tre/Leu/Sal samples, processed under either "A" or "B" conditions and stored at 25° C./50% RH resulted in extreme agglomeration (represented by an N/A) due to an uptake of moisture resulting in total physical loss of primary particles e.g. agglomeration induced through amorphous crystallisation. Only Tau/Leu/Sal samples (FIG. 16) stored at 25° C./50% RH (process B) resulted in measurable PSD values. Furthermore these values ($D_{10}$, $D_{50}$ and $D_{90}$) were all <10 μm.

Example 3

Preparation of Glycopyrronium Bromide/Taurine/L-Leucine Samples:

Glycopyrronium bromide (1.0% w/w), raw taurine (96.5% w/w) and L-Ieucine (2.5% w/w) samples were dissolved in Milli-Q water (60 mL) and sonicated. The prepared feedstock solution was spray dried using a laboratory spray dryer using a 0.5 mm, two fluid nozzle, 48.0 L·$min^{-1}$ atomisation flow rate, 25.5 kg·$hr^{-1}$ drying gas flow rate, 60.0° C. outlet temperature and 5.0 g·$min^{-1}$ feed rate. Spray drying parameters identified as appropriate for producing taurine particles suitable for inhalation.

Preparation of Glycopyrronium Bromide/Trehalose/L-Leucine Samples:

Glycopyrronium bromide (1.0% w/w), raw trehalose dihydrate (89.0% w/w in the dried product) and L-leucine (10.0% w/w) samples were dissolved in Milli-Q water (100 mL) and sonicated. The prepared feedstock solution was spray dried using a laboratory spray dryer using a 0.5 mm, two fluid nozzle, 42.0 L·$min^{-1}$ atomisation flow rate, 18.0 kg·$hr^{-1}$ drying gas flow rate, 70.0° C. outlet temperature and 2.0 g·$min^{-1}$ feed rate. Spray drying parameters identified as appropriate for producing taurine particles suitable for inhalation.

Conditioning of Samples

The taurine based formulation was stored in an open jar at ambient conditions overnight to condition the samples prior to analysis.

The trehalose based formulation was stored in a sealed jar under low humidity (<5% RH) prior to analysis.

Each formulation was assessed for PSD, KF and assay/content at the initial time point. For the taurine sample this corresponds to the powder after storage in an open jar at ambient conditions overnight. For trehalose this corresponds to the powder after storage overnight in a sealed jar under low humidity (<5% RH).

Each formulation was then assessed for PSD and drug content after 24 hours storage open at a constant relative humidity (% RH) of 53% RH and 23±3° C.

Particle Size Distribution (PSD)

Particle size distributions of the samples were measured by laser diffraction using a Sympatec HELOS and RODOS particle size analyser and ASPIROS dispersion unit (1.0 bar dispersion). A focal length corresponding to R4 lens was used and each batch sample was run in triplicate in order to determine the average particle size. In this instance, the $D_{90}$ for each batch sample was derived from the diffraction data using in built Sympatec software (WINDOX 5.0).

Moisture Content by Karl Fischer (KF)

Karl Fischer (KF) analysis is used to assess the water content of solid formulations using the Metrohm 774 Oven Sample Processor and 756KF Coulometer. The solid formulations were heated to a set temperature of 120.0° C. and titrated using the coulometer until no water is remaining in the sample. 10 mg of each powder was weighed and the samples assessed. This was performed on both the taurine and trehalose based formulations.

Aerosol Performance Testing

The Fast Screening Impactor (FSI) was used to assess the aerosolisation properties of the powder. Each formulation was assessed using gravimetric analysis, which involved filling a blister with the formulation (12.5±1.0 mg) and firing into the FSI. The mass of the powder evacuated from the blister and the mass collected on the fine fraction collector filter paper can then be calculated to evaluate how well the formulation is aerosolised. Water was used as the diluent for the insert.

Drug Content Assay

The drug content of the taurine and trehalose based formulations were assessed using High Performance Liquid Chromatography (HPLC) at the initial time point and after 24 hours to assess the chemical stability of the formulations.

All data is summarised in table 6.

TABLE 6

Summarises the data for glycopyrronium bromide T = 0, 24 hours and 27 days

| Formulation/ Condition | Time point | Mean D10 (μm) | Mean D50 (μm) | Mean D90 (μm) | Drug Assay (% Nominal) | % FPF <5 μm t = 0 | KF (% w/w) |
|---|---|---|---|---|---|---|---|
| Trehalose/ glycopyrronium bromide | Initial | 0.73 | 1.65 | 3.43 | 103.1 | 70.2 | 2.59 |
| | 24 hours at 53% RH | No result - solid compact formed, mechanical force required to break up compact | | | 91.2 | | |
| | 27 days at ambient | | | | | | |

TABLE 6-continued

Summarises the data for glycopyrronium bromide T = 0, 24 hours and 27 days

| Formulation/ Condition | Time point | Mean D10 (μm) | Mean D50 (μm) | Mean D90 (μm) | Drug Assay (% Nominal) | % FPF <5 μm t = 0 | KF (% w/w) |
|---|---|---|---|---|---|---|---|
| Taurine/ glycopyrronium bromide | Initial | 0.76 | 1.79 | 4.02 | 100.7 | 40.3 | 0.41 |
| | 24 hours at 53% RH | 0.77 | 1.87 | 4.27 | 98.6 | | |
| | 27 days at ambient | 0.77 | 1.85 | 4.23 | | | |

Table 6 demonstrates that both taurine and trehalose based formulations are aerosolisable and respirable at the initial time point.

After 24 hours storage at 53% RH the trehalose formulation has agglomerated and is no longer respirable, a PSD assessment was not able to be performed due to the formation of a solid compact. Additionally, the drug content dropped from 103% of nominal to 91% of nominal, indicating this is not chemically stable. Whereas, after 24 hours storage at 53% RH the taurine formulation has remained respirable ($D_{90}$<10 μm), and is chemically stable. After 27 days storage at ambient conditions the taurine particles remain respirable and aerosolisable.

Example 4

Preparation of Salbutamol Sulphate/Taurine/L-Leucine Samples:

Salbutamol sulphate (1.0% w/w), raw taurine (96.5% w/w) and L-leucine (2.5% w/w) samples were dissolved in Milli-Q water (60 mL) and sonicated. The prepared feedstock solution was spray dried using a spray dryer using a 0.5 mm, two fluid nozzle, 48.0 L·min$^{-1}$ atomisation flow rate, 25.5 kg·hr$^{-1}$ drying gas flow rate, 60.0° C. outlet temperature and 5.0 g·min$^{-1}$ feed rate. Spray drying parameters identified as appropriate for producing taurine particles suitable for inhalation.

The taurine based formulation was stored in an open jar at ambient conditions overnight to condition the samples.

The formulation was assessed for PSD, KF and assay/content at the initial time point.

The formulation was then assessed for PSD and drug content after 24 hours storage open at a constant relative humidity (% RH) of 53% RH and 23±3° C.

Particle Size Distribution (PSD)

Particle size distributions of the samples were measured by laser diffraction using a Sympatec HELOS and RODOS particle size analyser and ASPIROS dispersion unit (1.0 bar dispersion). A focal length corresponding to R4 lens was used and each batch sample was run in triplicate in order to determine the average particle size. In this instance, the $D_{90}$ for each batch sample was derived from the diffraction data using in built Sympatec software (WINDOX 5.0).

Moisture Content by Karl Fischer (KF)

Karl Fischer (KF) analysis is used to assess the water content of solid formulations using the Metrohm 774 Oven Sample Processor and 756KF Coulometer. The solid formulations were heated to a set temperature of 120.0° C. and titrated using the coulometer until no water is remaining in the sample. 10 mg of each powder was weighed and the samples assessed.

Aerosol Performance Testing

The Fast Screening Impactor (FSI) was used to assess the aerosolisation properties of the powder. Each formulation was assessed using gravimetric analysis, which involved filling a blister with the formulation (12.5±1.0 mg) and firing into the FSI. The mass of the powder evacuated from the blister and the mass collected on the fine fraction collector filter paper can then be calculated to evaluate how well the formulation is aerosolised. Water was used as the diluent for the insert.

Drug Content Assay

The drug content of the taurine based formulation was assessed using High Performance Liquid Chromatography (HPLC) at the initial time point and after 24 hours to assess the chemical stability of the formulation.

All data is summarised in Table 7.

TABLE 7

Summarises the data for salbutamol sulphate T = 0 and T = 24 hours

| Formulation/ Condition | Time point | Mean D10 (μm) | Mean D50 (μm) | Mean D90 (μm) | Drug Assay (% Nominal) | % FPF <5 μm t = 0 | KF (% w/w) |
|---|---|---|---|---|---|---|---|
| Taurine, Salbutamol sulphate | Initial | 0.77 | 1.87 | 4.26 | 97.9 | 42.0 | 0.5 |
| | 24 hours at 53% RH | 0.78 | 1.92 | 4.38 | 99.4 | | |
| | 26 days at ambient | 0.78 | 1.92 | 4.38 | | | |

Table 7 demonstrates that the taurine based formulation is aerosolisable and respirable at the initial time point. After 24 hours storage at 53% RH the taurine formulation remains respirable ($D_{90}$<10 μm) and chemically stable. After 26 days at storage at ambient conditions the taurine formulation remains respirable and aerosolisable.

Example 5

Preparation of Sumatriptan Succinate/Taurine/L-Leucine Samples:

Sumatriptan succinate (1.0% w/w), raw taurine (96.5% w/w) and L-leucine (2.5% w/w) samples were dissolved in Milli-Q water (60 mL) and sonicated. The prepared feedstock solution was spray dried using a spray dryer using a 0.5 mm, two fluid nozzle, 48.0 L·min$^{-1}$ atomisation flow rate, 25.5 kg·hr$^{-1}$ drying gas flow rate, 60.0° C. outlet temperature and 5.0 g·min$^{-1}$ feed rate. Spray drying parameters identified as appropriate for producing taurine particles suitable for inhalation.

The taurine based formulation was stored in an open jar at ambient conditions overnight to condition the samples.

The formulation was assessed for PSD, KF and assay/content at the initial time point.

The formulation was then assessed for PSD and drug content after 24 hours storage open at a constant relative humidity (% RH) of 53% RH and 23±3° C.

Particle Size Distribution (PSD)

Particle size distributions of the samples were measured by laser diffraction using a Sympatec HELOS and RODOS particle size analyser and ASPIROS dispersion unit (1.0 bar dispersion). A focal length corresponding to R4 lens was used and each batch sample was run in triplicate in order to determine the average particle size. In this instance, the $D_{90}$ for each batch sample was derived from the diffraction data using in built Sympatec software (WINDOX 5.0).

Moisture Content by Karl Fischer (KF)

Karl Fischer (KF) analysis is used to assess the water content of solid formulations using the Metrohm 774 Oven Sample Processor and 756KF Coulometer. The solid formulations were heated to a set temperature of 120.0° C. and titrated using the coulometer until no water is remaining in the sample. 10 mg of each powder was weighed and the samples assessed.

Aerosol Performance Testing

The Fast Screening Impactor (FSI) was used to assess the aerosolisation properties of the powder. Each formulation was assessed using gravimetric analysis, which involved filling a blister with the formulation (12.5±1.0 mg) and firing into the FSI. The mass of the powder evacuated from the blister and the mass collected on the fine fraction collector filter paper can then be calculated to evaluate how well the formulation is aerosolised. Water was used as the diluent for the insert.

Drug Content Assay

The drug content of the taurine based formulations was assessed using ultraviolet (U.V.) analysis at the initial time point and after 24 hours to assess the chemical stability of the formulation.

TABLE 8

Summarises the data for sumatriptan succinate T = 0 and T = 24 hours

| Formulation/ Condition | Time point | Mean D10 (μm) | Mean D50 (μm) | Mean D90 (μm) | Drug Assay (% Nominal) | % FPF <5 μm t = 0 | KF |
|---|---|---|---|---|---|---|---|
| Taurine, Sumatriptan succinate | Initial | 0.77 | 1.89 | 4.31 | 97.0 | 53.9 | 0.48 |
| | 24 hours at 53% RH | 0.78 | 1.94 | 4.43 | 93.8 | | |
| | 26 days at ambient | 0.78 | 1.92 | 4.39 | | | |

Table 8 demonstrates that the taurine based formulation is aerosolisable and respirable at the initial time point, with sumatriptan succinate present. After 24 hours storage at 53% RH the taurine formulation remains aerosolisable and respirable ($D_{90}$<10 μm) and chemically intact. After 26 days at storage at ambient conditions the taurine formulation remains respirable and aerosolisable.

Dose Ranging Study

Preparation of Salbutamol Sulphate/Taurine/L-Leucine Samples:

Salbutamol sulphate, raw taurine and L-leucine samples were dissolved in the ratios detailed in Milli-Q water (60 mL) and sonicated. The prepared feedstock solution was spray dried using a spray dryer using a 0.5 mm, two fluid nozzle, 48.0 L·min$^{-1}$ atomisation flow rate, 25.5 kg·hr$^{-1}$ drying gas flow rate, 60.0° C. outlet temperature and 5.0 g·min$^{-1}$ feed rate. Spray drying parameters identified as appropriate for producing taurine particles suitable for inhalation.

The taurine based formulation was stored in an open jar at ambient conditions overnight to condition the samples.

The formulations were assessed for PSD, KF and assay/content at the initial time point.

The formulations was then assessed for PSD and drug content after 24 hours storage open at a constant relative humidity (% RH) of 53% RH and 23±3° C.

TABLE 9

Formulation composition and data for salbutamol sulphate at a range of compositions T = 0 and T = 24 hours

| Formulation/ Condition | Time point | Mean D10 (μm) | Mean D50 (μm) | Mean D90 (μm) | % FPF <5 μm | Drug Assay (% Nominal) | KF |
|---|---|---|---|---|---|---|---|
| Taurine 96.5% w/w, leucine 2.5% w/w, drug 1.0% w/w | Initial | 0.77 | 1.87 | 4.26 | 42.0 | 97.9 | 0.5 |
| | 24 hours At 53% RH | 0.78 | 1.92 | 4.38 | | 99.4 | |
| Taurine 87.5% w/w, Leucine 2.5% w/w, drug 10.0% w/w | Initial | 0.88 | 2.55 | 5.92 | 35.1 | 96.8 | 1.45 |
| | 60 hours At 53% RH | 0.96 | 2.93 | 6.52 | | 97.8 | |
| Taurine 79.95% w/w, Leucine 2.5% w/w, drug 17.55% w/w | Initial | 1.02 | 3.21 | 6.93 | 39 | 97.7 | 1.27 |
| | 24 hours At 53% RH | 1.01 | 3.23 | 12.06 | | 97.2 | |
| Taurine 77.0% w/w, Leucine 2.5% w/w, drug 20.5% w/w | Initial | 1.26 | 3.87 | 7.75 | 33 | 97.0 | 0.15 |
| | 24 hours At 53% RH | 2.38 | 5.4 | 94.59 | | 99.6 | |
| Taurine 73.1% w/w, Leucine 2.5% w/w, drug 24.4% w/w | Initial | 3.15 | 7.06 | 80.64 | 25 | 95.3 | |
| | 24 hours At 53% RH | 2.8 | 6.74 | 86.62 | | 95.9 | |

Table 9 shows that as the taurine concentration in the formulation decreases and the drug concentration increases the physically stabilising influence of taurine begins to diminish.

There is no agglomeration of the powder when left at ambient overnight and at 53% RH (21±3° C.) for 24 hours at taurine concentrations of 96.5% w/w and 87.5% w/w. A small amount of agglomeration is observed (n=1 rep) at 79.95% w/w taurine concentration. A larger amount of agglomeration is observed at taurine concentrations above 77.0% w/w.

Example 6, pMDI

Preparation of Salbutamol Sulphate/Raurine/L-Leucine Samples:

Salbutamol sulphate, raw taurine and L-leucine samples were dissolved in the ratios detailed in Table 10. Milli-Q water (60 mL) and sonicated. The prepared feedstock solution was spray dried using a spray dryer using a 0.5 mm, two fluid nozzle, 48.0 L·min$^{-1}$ atomisation flow rate, 25.5 kg·hr$^{-1}$ drying gas flow rate, 60.0° C. outlet temperature and 5.0 g·min$^{-1}$ feed rate. Spray drying parameters identified as appropriate for producing taurine particles suitable for inhalation.

The taurine based formulation was stored in an open jar at ambient conditions overnight to condition the samples.

Preparation of Salbutamol/Taurine/L-leucine Metered Dose Inhalers:

Formulations as listed in table 10 were weighed into 19 mL Presspart aluminium canisters. A Bespak 357 50 μL valve was crimped onto the cannister. P134a propellant was subsequently filled through the valve using a Pamasol pressure fill system. The filled can was placed into a Bespak Actuator with nominal orifice size of 0.42 mm.

Emitted Dose

Prior to testing the MDI canister was placed in a Branson 8510 model sonic bath for five minutes. Dose Uniformity Sampling Apparatus (DUSA) with a testing flow rate of 28.3 $L \cdot min^{-1}$ was used to assess the emitted dose from the MDI. Ten actuations from the MDI were fired into individual DUSA. The DUSA tubes were rinsed with fixed volumes of diluent to recover the salbutamol sulphate. Samples were analysed using High Performance Liquid Chromatography (HPLC). The mean emitted dose was calculated as the average recovery from ten DUSA.

Particle Size Distribution of Emitted Dose

Prior to testing the MDI canister was placed in a Branson 8510 model sonic bath for five minutes. The Next Generation Impactor (NGI) with a testing flow rate of 30 $L \cdot min^{-1}$ was used to assess the particle size distribution of the emitted dose from the MDI. Two actuations from the MDI were fired into the NGI. The MDI actuator, NGI throat and stages were washed with fixed volumes of diluent to recover the salbutamol sulphate. Samples were analysed using High Performance Liquid Chromatography (HPLC). The Impactor Sized Mass (ISM, the sum of the recovered dose on stages 2 to the micro orifice collector of the NGI) was calculated as a function of the emitted dose (i.e. the ratio between the ISM and the sum of the ISM, throat and stage 1 deposition expressed as a percentage). The Mass Median Aerodynamic Diameter was determined.

Drug Content Assay

The drug content of the salbutamol sulphate in propellant in the MDI canister was determined. Canisters were submersed in liquid nitrogen to freeze propellant. An incision made in the valve shoulder allowed the propellant to sublime as the MDI equilibrated to room temperature. The canister and valve were rinsed with fixed volumes of diluent to recover the salbutamol sulphate. Samples were analysed using High Performance Liquid Chromatography (HPLC).

Particle Size Distribution (PSD)—Prior to Use in MDI Preparation

Approximately 10 mg of formulation was dispersed in 0.2% lecithin in iso-octane and sonicated for 3 minutes using a sonic probe. The sample was left to rest for 5 minutes then analysed for particle size distribution using the Malvern Mastersizer 2000, with a pump speed of 3000 rpm and an obscuration of 5-10%. 6 measurements were taken for each sample and the mean $D_{10}$, $D_{50}$ and $D_{90}$ determined using the built in Malvern software.

Particle Size Distribution (PSD)—after Use in MDI Preparation

Prior to testing the MDI canister was placed in a Branson 8510 model sonic bath for five minutes. Canisters were submersed in liquid nitrogen to freeze propellant. An incision made in the valve shoulder allowed the propellant to sublime as the MDI equilibrated to room temperature. Formulation was manually recovered from the canister. Approximately 10 mg of formulation was dispersed in 0.2% lecithin in iso-octane and sonicated for 3 minutes using a sonic probe. The sample was left to rest for 5 minutes then analysed for particle size distribution using the Malvern Mastersizer 2000, with a pump speed of 3000 rpm and an obscuration of 5-10%. 6 measurements were taken for each sample and the mean D10, D50 and D90 determined using the built in Malvern software.

Visual Inspection of MDI Suspensions

Formulations as listed in table 11 were weighed into plastic coated clear glass canisters. A continuous flow valve was crimped onto the canister. P134a propellant was subsequently filled through the valve using a Pamasol pressure fill system. Prior to testing the MDI canister was placed in a Branson 8510 model sonic bath for five minutes. Each canister was shaken for ten seconds and placed in front of a black background. Photographs were taken at 5 second intervals. Visual comparison of the photographs versus a clear glass canister allowed determination of the time where the majority of the formulation was no longer in suspension. No creaming was visible for any of the suspensions.

TABLE 10

Formulation composition for salbutamol sulphate in a range of MDI compositions

| Formulation/ Condition | Formulation per canister (mg) | HFA 134a per canister (mg) |
|---|---|---|
| Taurine 87.5% w/w, Leucine 2.5% w/w, Salbutamol Sulphate 10.0% w/w | 120 | 14700 |
| Taurine 73.1% w/w, Leucine 2.5% w/w, Salbutamol Sulphate 24.4% w/w | 48 | 14700 |
| Taurine 90% w/w, Salbutamol Sulphate 10.0% w/w | 120 | 14700 |
| Taurine 100% w/w | 48 | 14700 |

TABLE 11

Formulation composition for salbutamol sulphate in a range of MDI composition

| Formulation/ Condition | Formulation per canister (mg) | HFA 134a per canister (mg) |
|---|---|---|
| Taurine 87.5% w/w, Leucine 2.5% w/w, Salbutamol Sulphate 10.0% w/w | 60 | 7350 |
| Taurine 73.1% w/w, Leucine 2.5% w/w, Salbutamol Sulphate 24.4% w/w | 24 | 7350 |
| Taurine 90% w/w, Salbutamol Sulphate 10.0% w/w | 60 | 7350 |
| Taurine 100% w/w | 24 | 7350 |

TABLE 12

Formulation composition for salbutamol sulphate in a range of MDI compositions

| Formulation/ Condition | Mean D10 Pre MDI (μm) | Mean D50 Pre MDI (μm) | Mean D90 Pre MDI (μm) | Mean D10 Ex MDI (μm) | Mean D50 Ex MDI (μm) | Mean D90 Ex MDI (μm) | Emitted Dose Mean (μg) (RSD, %) | Visible Suspension Duration (s) | Impactor Sized Mass (% of Emitted Dose) | MMAD (μm) | Drug Assay (% Nominal) |
|---|---|---|---|---|---|---|---|---|---|---|---|
| Taurine 87.5% w/w, Leucine 2.5% w/w, Salbutamol Sulphate 10.0% w/w | 1.0 | 2.9 | 6.5 | 1.0 | 2.9 | 6.6 | 50.0 (32.2) | 15 | 33.9 | 7.10 | 102 |
| Taurine 73.1% w/w, Leucine 2.5% w/w, Salbutamol Sulphate 24.4% w/w | 1.2 | 5.8 | 36.0 | 1.1 | 5.7 | 15.0 | 81.3 (13.0) | >120 | 13.5 | Not Determined | 102 |

TABLE 12-continued

Formulation composition for salbutamol sulphate in a range of MDI compositions

| Formulation/ Condition | Mean D10 Pre MDI (µm) | Mean D50 Pre MDI (µm) | Mean D90 Pre MDI (µm) | Mean D10 Ex MDI (µm) | Mean D50 Ex MDI (µm) | Mean D90 Ex MDI (µm) | Emitted Dose Mean (µg) (RSD, %) | Visible Suspension Duration (s) | Impactor Sized Mass (% of Emitted Dose) | MMAD (µm) | Drug Assay (% Nominal) |
|---|---|---|---|---|---|---|---|---|---|---|---|
| Taurine 90% w/w, Salbutamol Sulphate 10.0% w/w | 1.0 | 3.5 | 7.4 | 1.0 | 3.8 | 7.8 | 46.3 (12.0) | 20 | 33.8 | 7.39 | 100 |
| Taurine 100% w/w | 1.1 | 2.9 | 5.9 | 1.1 | 2.8 | 5.5 | | 15 | | | |

The invention claimed is:

1. A method for producing conditioned taurine in a dry powder form suitable for inhalation obtained by a method comprising providing a feedstock comprising taurine in an aqueous solution or suspension for spray drying, wherein the feedstock concentration of taurine in g $mL^{-1}$ is between 0.001 g $mL^{-1}$ and 0.1 g $mL^{-1}$;

selecting a maximum target particle size, measured as $D_{90}$, in µm of particles produced by the spray drying, wherein the maximum target particle size is 20 µm or less;

selecting the feed rate in mL $min^{-1}$ or the volume of drying gas in g $min^{-1}$, wherein the feed rate is of from 1.5 mL $min^{-1}$ to 4.5 mL $min^{-1}$ and the volume of drying gas is of from 200 g $min^{-1}$ to 250 g $min^{-1}$;

determining the feed rate or the volume of drying gas that was not selected in the preceding step such that it satisfies equation (I):

$$\text{maximum target particle size} \geq 6.8 + 3450.4X - 6230437.9X^2 \quad \text{(I)}$$

wherein $$X = \frac{(\text{feedstock concentration of taurins}) \times (\text{feed rate})}{(\text{volume of drying gas})};$$

and spray drying the feedstock to yield particles using the feed rate and volume of drying gas selected and determined in the preceding two steps.

2. The method of claim 1, wherein the method further comprises at least one parameter selected from the group consisting of:

(a) the pH of the feedstock is between pH 1 and pH 7, (b) the feedstock temperature is between 0.1° C. and 100° C., (c) the outlet temperature of the spray drying apparatus is between 50° C. and 120° C., (d) X is between $2.00 \times 10^{-6}$ and $2.75 \times 10^{-3}$, (e) the feedstock concentration of taurine is between 0.01 g $mL^{-1}$ and 0.05 g $mL^{-1}$, and (f) any combination thereof.

3. The method of claim 1, wherein the method further comprises at least one parameter selected from the group consisting of:

(a) the pH of the feedstock is at or below pH 4, (b) the feedstock temperature is between 20° C. and 70° C., (c) the outlet temperature of the spray drying apparatus is between 60° C. and 100° C., (d) X is between $2.00 \times 10^{-6}$ and $2.75 \times 10^{-3}$, (e) the feedstock concentration of taurine is between 0.01 g $mL^{-1}$ and 0.05 g $mL^{-1}$, and (f) any combination thereof.

4. The method of claim 1, wherein the feedstock further comprises an amino acid.

5. The method of claim 4, wherein the amino acid is selected from the group consisting of alanine, leucine, isoleucine, lysine, valine, methionine and phenylalanine.

6. The method of claim 5, wherein the amino acid is leucine.

7. The method of claim 1, wherein the feedstock further comprises a medicament.

8. The method of claim 7, wherein the medicament is selected from the group consisting of budesonide, formoterol fumarate dihydrate, tiotropium, fluticasone propionate, salmeterol xinafoate, vilanterol trifenatate, umeclidinium bromide, glycopyrronium bromide, indacaterol maleate and any combinations thereof.

9. The method of claim 4, wherein the feedstock further comprises a medicament.

10. The method of claim 9, wherein the medicament is selected from the group consisting of budesonide, formoterol fumarate dihydrate, tiotropium, fluticasone propionate, salmeterol xinafoate, vilanterol trifenatate, umeclidinium bromide, glycopyrronium bromide, indacaterol maleate and any combinations thereof.

11. The method of claim 2, wherein the feedstock further comprises an amino acid.

12. The method of claim 11, wherein the amino acid is selected from the group consisting of alanine, leucine, isoleucine, lysine, valine, methionine and phenylalanine.

13. The method of claim 12, wherein the amino acid is leucine.

14. The method of claim 2, wherein the feedstock further comprises a medicament.

15. The method of claim 14, wherein the medicament is selected from the group consisting of budesonide, formoterol fumarate dihydrate, tiotropium, fluticasone propionate, salmeterol xinafoate, vilanterol trifenatate, umeclidinium bromide, glycopyrronium bromide, indacaterol maleate and any combinations thereof.

16. The method of claim 3, wherein the feedstock further comprises an amino acid.

17. The method of claim 16, wherein the amino acid is selected from the group consisting of alanine, leucine, isoleucine, lysine, valine, methionine and phenylalanine.

18. The method of claim 17, wherein the amino acid is leucine.

19. The method of claim 3, wherein the feedstock further comprises a medicament.

20. The method of claim 19, wherein the medicament is selected from the group consisting of budesonide, formoterol fumarate dihydrate, tiotropium, fluticasone propionate, salmeterol xinafoate, vilanterol trifenatate, umeclidinium bromide, glycopyrronium bromide, indacaterol maleate and any combinations thereof.

* * * * *